(12) United States Patent
Yamakawa et al.

(10) Patent No.: US 8,431,676 B2
(45) Date of Patent: Apr. 30, 2013

(54) AROMATIC COMPOUND AND SULFONATED POLYARYLENE POLYMER

(75) Inventors: Yoshitaka Yamakawa, Chuo-ku (JP); Yousuke Konno, Chuo-ku (JP); Teruhiko Umehara, Chuo-ku (JP)

(73) Assignee: JSR Corporation, Tokyo (JP)

( * ) Notice: Subject to any disclaimer, the term of this patent is extended or adjusted under 35 U.S.C. 154(b) by 504 days.

(21) Appl. No.: 12/298,385

(22) PCT Filed: Apr. 24, 2007

(86) PCT No.: PCT/JP2007/058856
§ 371 (c)(1),
(2), (4) Date: Oct. 24, 2008

(87) PCT Pub. No.: WO2007/125919
PCT Pub. Date: Nov. 8, 2007

(65) Prior Publication Data
US 2010/0174042 A1 Jul. 8, 2010

(30) Foreign Application Priority Data

Apr. 25, 2006 (JP) .................................. 2006-121081

(51) Int. Cl.
*C08G 8/02* (2006.01)
(52) U.S. Cl.
USPC ........................................................ 528/125
(58) Field of Classification Search ............... 528/85, 528/125
See application file for complete search history.

(56) References Cited

U.S. PATENT DOCUMENTS

| | | | |
|---|---|---|---|
| 5,403,675 | A | 4/1995 | Ogata et al. |
| 6,794,480 | B2 | 9/2004 | Goto et al. |
| 6,812,290 | B2 | 11/2004 | Goto et al. |
| 7,163,988 | B2 | 1/2007 | Rozhanskii et al. |
| 2004/0044166 | A1 | 3/2004 | Rozhanskii et al. |
| 2007/0117872 | A1* | 5/2007 | Kawai et al. ............. 521/27 |

FOREIGN PATENT DOCUMENTS

| | | |
|---|---|---|
| JP | 2-159 | 1/1990 |
| JP | 2001-342241 | 12/2001 |
| JP | 2002-37986 | 2/2002 |
| JP | 2002-220530 | 8/2002 |
| JP | 2002-293889 | 10/2002 |
| JP | 2004-137444 | 5/2004 |
| JP | 2004-346163 | 12/2004 |
| JP | 2005-36125 | 2/2005 |
| JP | 2005-60585 | 3/2005 |
| JP | 2005-60625 | 3/2005 |
| JP | 2006-176682 | 7/2006 |
| JP | 2006-228628 | 8/2006 |

OTHER PUBLICATIONS

Douglas W. Lowman, et al., "Magnetic Resonance Spectroscopic Investigations of Poly(p-Phenylene Sulfide/Disulfide), PPS/DS", Bulletin of Magnetic Resonance, vol. 14, Nos. 1-4, 1992, 6 Pages.
R. A. Clendinning, et al., "Poly (aryl ether ketone) block and chain-extended copolymers. 1. Preparation and characterization of a new class of functional poly(aryl ether ketone) oligomers", Macromolecules, vol. 26, No. 9, 1993, pp. 2361-2365.
S. C. Dhanesar, et al., "Synthesis and chromatographic properties of cyanophenyl ethers", Journal of Chromatography, vol. 252, 1982, pp. 91-99.

* cited by examiner

*Primary Examiner* — Shane Fang
(74) *Attorney, Agent, or Firm* — Oblon, Spivak, McClelland, Maier & Neustadt, L.L.P.

(57) ABSTRACT

The invention described herein relates to a polyarylene copolymer comprising a structural unit represented by formula (1'):

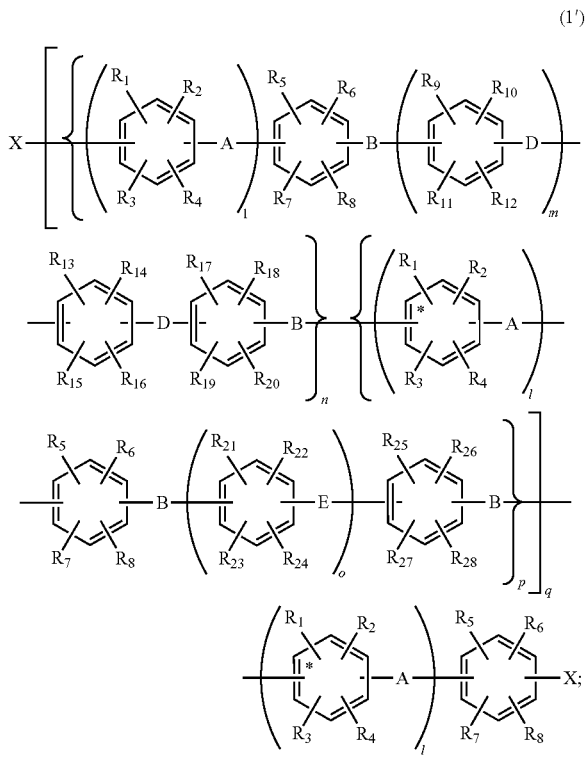

where the structural variables are defined herein. The invention also relates to a solid polymer electrolyte, a proton conductive membrane and A proton conductive membrane for direct methanol fuel cell which contains the polyarylene copolymer.

17 Claims, No Drawings

AROMATIC COMPOUND AND SULFONATED POLYARYLENE POLYMER

FIELD OF THE INVENTION

The present invention relates to aromatic compounds and sulfonated polyarylenes.

BACKGROUND OF THE INVENTION

Solid electrolytes have recently been used more often than (aqueous) electrolyte solutions. This tendency is firstly because those solid electrolytes have good processability in application in electric and electronic materials, and secondly because of the transitions to overall size and weight reduction and electric power saving.

Inorganic and organic proton conductive materials are known.

As the inorganic materials, hydrates such as uranyl phosphate are used. However, it is difficult that the inorganic materials are enough contacted with substrate or electrode interface. As a result, many problems in forming a conductive layer on a substrate or an electrode are caused.

On the other hand, the organic materials include polymers that belong to cation exchange resins, with examples including sulfonated vinyl polymers such as polystyrenesulfonic acid; perfluoroalkylsulfonic acid polymers and perfluoroalkylcarboxylic acid polymers represented by Nafion® (manufactured by DuPont); and polymers obtained by introducing sulfonic acid groups or phosphoric acid groups in heat resistant polymers such as polybenzimidazole and polyether ether ketone.

In the manufacturing of fuel cells, an electrolyte membrane of the perfluoroalkylsulfonic acid polymer is sandwiched between electrodes and heat processed by hot pressing or the like to give a membrane-electrode assembly. The fluorine-containing electrolyte membranes are thermally deformed at relatively low temperatures around 80° C. and can be assembled easily. However, the temperature can rise to 80° C. or above by reaction heat during operation of the fuel cells. In this case, the electrolyte membrane is softened and creeps to cause short circuits between the electrodes, resulting in power generation failure.

To prevent these problems, the thickness of the electrolyte membranes is increased to a certain level or fuel cells are designed such that the power generation temperature will not exceed 80° C. Consequently, the maximum output of power generation is limited.

To solve the problems with low thermal deformation temperature and poor mechanical characteristics at high temperatures of the perfluoroalkylsulfonic acid polymers, solid polymer electrolyte membranes that have aromatic polymers used in engineering plastics have been developed.

For example, U.S. Pat. No. 5,403,675 (Patent Document 1) discloses solid polymer electrolytes comprising a rigid-rod sulfonated polyphenylene. The polymer is obtained by synthesizing a polymer of an aromatic compound composed of phenylene units, and then introducing a sulfonic acid group by reaction with a sulfonating agent. The electrolyte membranes of this polymer have a thermal deformation temperature of 180° C. or above and are excellent in creeping resistance at high temperatures. However, they require a very high temperature when assembled with electrodes by hot pressing. Long heating at high temperatures induces elimination reaction of the sulfonic acid groups, crosslinking among the sulfonic acid groups, and degradation of electrode layers.

Further, they are insufficient in properties for use as proton conductive membranes in direct methanol fuel cells.

Patent Document 1: U.S. Pat. No. 5,403,675

DISCLOSURE OF THE INVENTION

Objects of the invention are to provide sulfonated polymers having excellent processability and methanol resistance, and to provide solid polymer electrolytes and proton conductive membranes from the sulfonated polymer that have high proton conductivity and excellent power generation performance.

The present inventors studied diligently to solve the aforementioned problems and have found that the above objects are achieved with sulfonated polyarylenes that contain a specific structural unit. The present invention has been completed based on the finding.

The present invention has the following aspects [1] to [8].

[1] An aromatic compound represented by Formula (1) below:

[Chem. 1]

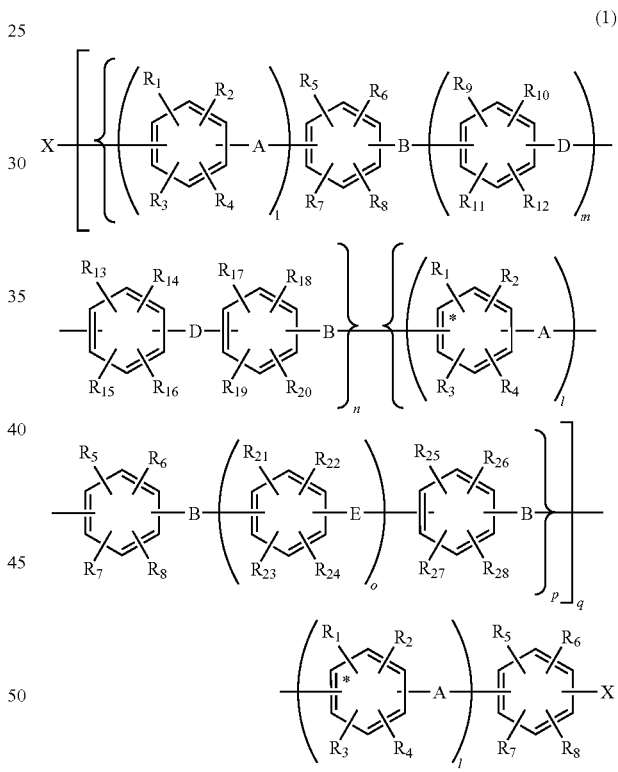

(1)

wherein A, D and E are each at least one structure selected from the group consisting of a direct bond, —O—, —S—, —CO—, —SO$_2$—, —SO—, —CONH—, —COO—, —(CF$_2$)$_f$— (wherein f is an integer of 1 to 10), —(CH$_2$)$_h$— (wherein h is an integer of 1 to 10), —CR'$_2$— (wherein R' is an aliphatic hydrocarbon group, an aromatic hydrocarbon group or a halogenated hydrocarbon group), a cyclohexylidene group and a fluorenylidene group;

each B is independently an oxygen atom or a sulfur atom;

X is an atom or a group selected from halogen atoms other than fluorine, —OSO$_2$CH$_3$ and —OSO$_2$CF$_3$;

R$_1$ to R$_{28}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group;

l and o are each an integer of 0 to 4; m is an integer of 1 to 4; q is an integer of 2 or greater; n and p indicate a composition ratio of the respective units and are each a number ranging from 0 to 1; n+p=1; and n is not 0.

[2] The compound described in [1], which is represented by Formula (2) below:

[Chem. 2]

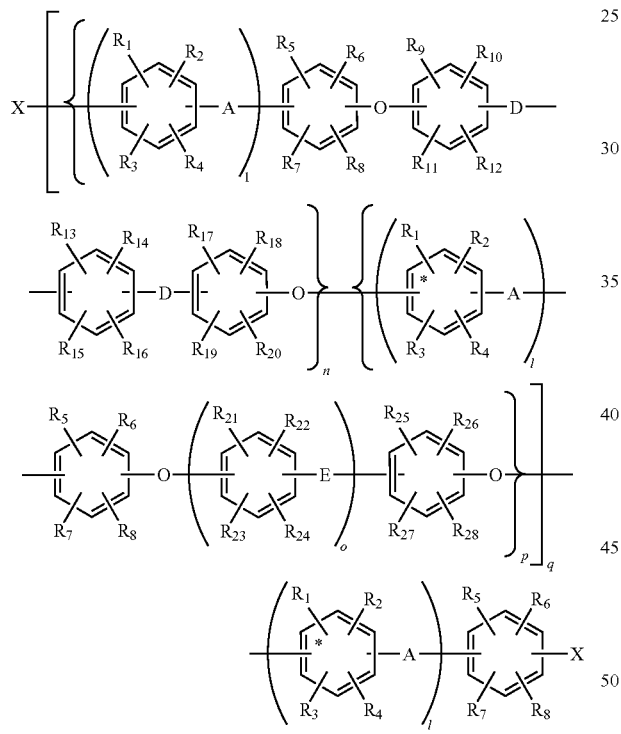

(2)

wherein A and E are each at least one structure selected from the group consisting of a direct bond, —O—, —CO—, —SO$_2$—, —SO—, —(CF$_2$)$_f$— (wherein f is an integer of 1 to 10), —(CH$_2$)$_h$— (wherein h is an integer of 1 to 10), —CR'$_2$— (wherein R' is an aliphatic hydrocarbon group, an aromatic hydrocarbon group or a halogenated hydrocarbon group), a cyclohexylidene group and a fluorenylidene group; D is a direct bond, —O—, —CO—, —(CH$_2$)$_h$— (wherein h is an integer of 1 to 10) or —CR''$_2$— (wherein R'' is an aliphatic hydrocarbon group or an aromatic hydrocarbon group); X is an atom selected from halogen atoms other than fluorine; R$_1$ to R$_{28}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group; l and o are each an integer of 0 to 4; q is an integer of 2 or greater; n and p indicate a composition ratio of the respective units and are each a number ranging from 0 to 1; n+p=1; and n is not 0.

[3] The compound described in [2], which is represented by Formula (3) below:

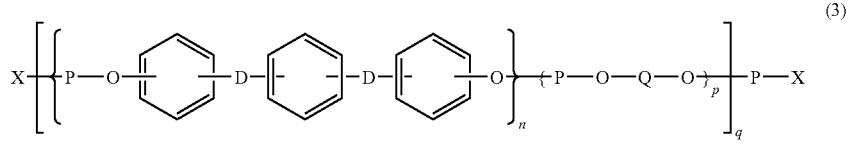

(3)

wherein X is an atom selected from halogen atoms other than fluorine; D is —O— or —CR''$_2$— (wherein R'' is an aliphatic hydrocarbon group or an aromatic hydrocarbon group); P is at least one structure selected from structures represented by Formulae (4-1) to (4-3) below; Q is at least one structure selected from structures represented by Formulae (5-1) to (5-12) below; q is an integer of 2 or greater; n and p indicate a composition ratio of the respective units and are each a number ranging from 0 to 1; n+p=1; and n is not 0.

[Chem. 4]

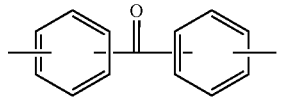

(4-1)

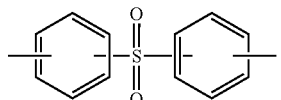

(4-2)

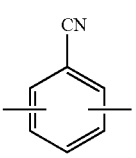

(4-3)

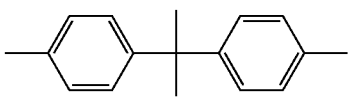

(5-1)

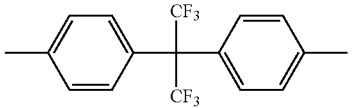

(5-2)

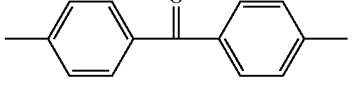

(5-3)

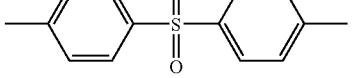

(5-4)

-continued

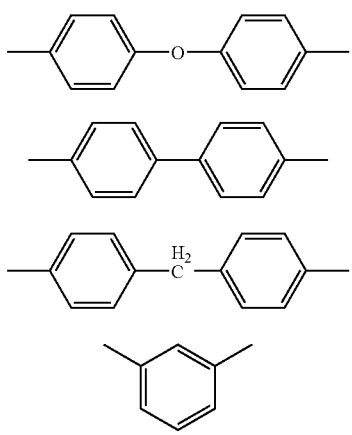

[4] The compound described in [3], wherein n in Formula (3) is 0.3 to 1.

[5] A polyarylene copolymer comprising a structural unit represented by Formula (1') below:

[Chem. 5]

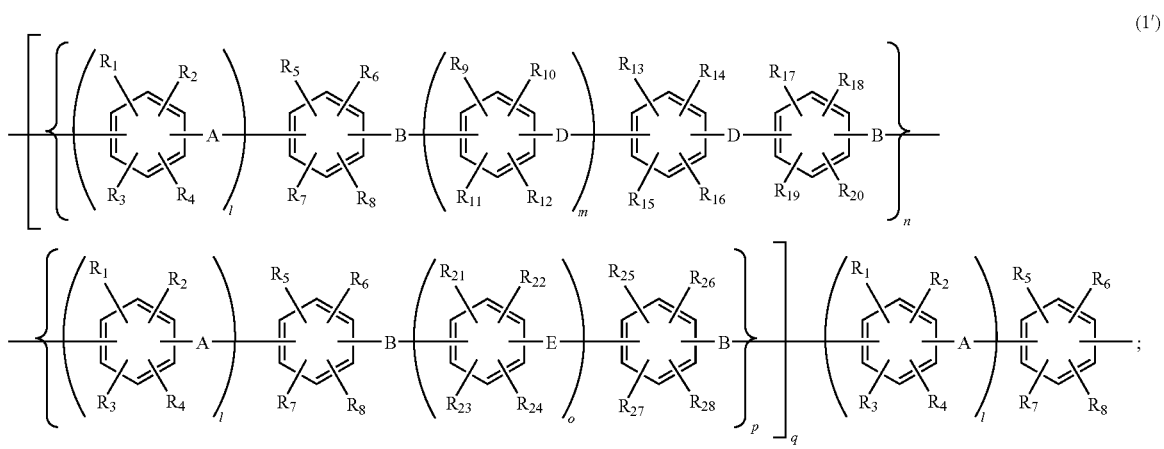

(1')

wherein A, D, E, B, $R_1$ to $R_{28}$, l, o, m, q, n and p are as defined in Formula (1).

[6] The polyarylene copolymer described in [5], which further comprises a structural unit represented by Formula (6) below:

[Chem. 6]

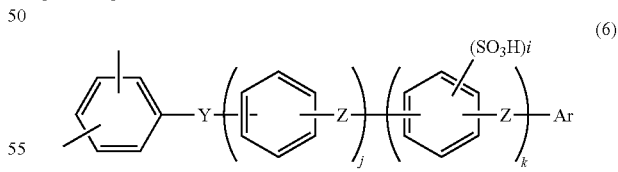

(6)

wherein Y is at least one structure selected from the group consisting of —CO—, —$SO_2$—, —SO—, —CONH—, —COO—, —$(CF_2)_f$— (wherein f is an integer of 1 to 10) and —$C(CF_3)_2$—; Z is at least one structure selected from the group consisting of a direct bond, —$(CH_2)_h$— (wherein h is an integer of 1 to 10), —$C(CH_3)_2$—, —O— and —S—; Ar is an aromatic group having a substituent represented by —$SO_3H$, —$O(CH_2)rSO_3H$ or —$O(CF_2)rSO_3H$; r is an integer of 1 to 12; j is an integer of 0 to 10; k is an integer of 0 to 10; and i is an integer of 1 to 4.

-continued

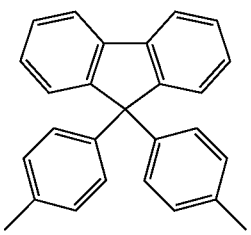

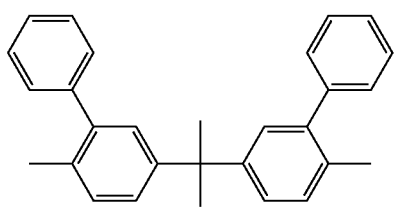

[7] A solid polymer electrolyte comprising the polyarylene copolymer of [6].

[8] A proton conductive membrane comprising the polyarylene copolymer of [6].

[9] A proton conductive membrane for direct methanol fuel cell comprising the polyarylene copolymer of [6].

ADVANTAGES OF THE INVENTION

The new aromatic compound of the invention has hydrophobic structural units which are derived from the compounds synthesized from a monomer that has three or more consecutive benzene rings such as 4,4'-(1,3-phenylenediiso- The aromatic compounds provide hydrophobic structural units. Therefore, even if polyarylene polymers, which are derived from said compounds, contain sulfonic acid groups in a high concentration, the polyarylene polymers can give polymer electrolytes and proton conductive membranes that have high methanol resistance, good processability and high proton conductivity.

If the sulfonic acid groups are introduced in a high concentration into compounds having two or less consecutive benzene rings, methanol resistance and processability are bad and bonding properties with electrodes may be lowered.

[Chem. 7]

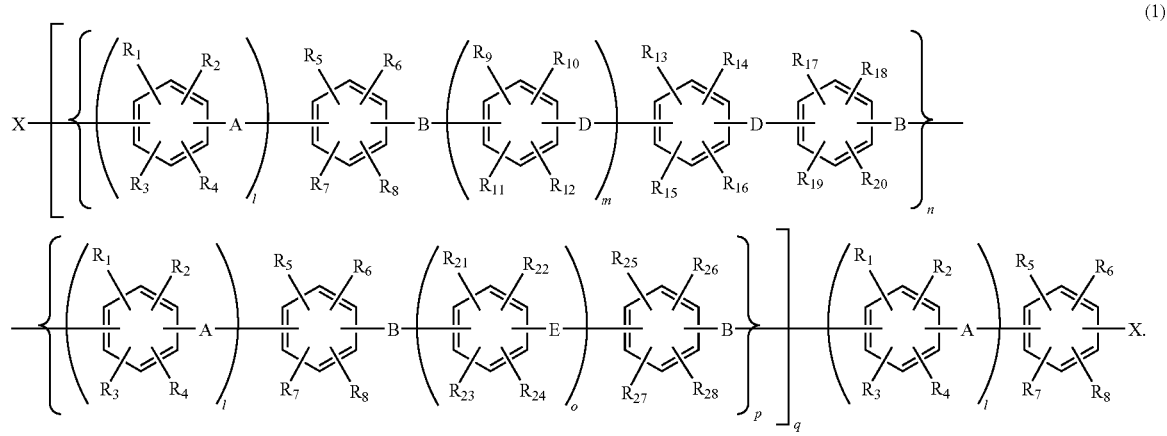

(1)

propylidene)bisphenol. Thereby, even if the sulfonic acid groups are introduced in a high concentration, the polyarylene polymers can give polymer electrolytes and proton conductive membranes that have high methanol resistance, good processability and high proton conductivity.

PREFERRED EMBODIMENTS OF THE INVENTION

The present invention will be described hereinbelow.

The compounds synthesized from a monomer that has three or more consecutive benzene rings such as 4,4'-(1,3-phenylenediisopropylidene)bisphenol, hydrophobic structural units derived from the compounds (hereinafter, "hydrophobic units"), polyarylene copolymers, sulfonated polyarylene copolymers, solid polymer electrolytes and proton conductive membranes will be described in detail.

[Aromatic Compounds]

The aromatic compounds according to the present invention are represented by Formula (1). The compounds are synthesized from a monomer that has three or more consecutive benzene rings such as 4,4'-(1,3-phenylenediisopropylidene)bisphenol. Monomer units having this skeleton form hydrophobic parts in polymers.

Because of containing three or more consecutive benzene rings represented by 4,4'-(1,3-phenylenediisopropylidene) bisphenol, the main chain skeleton is flexible and the thermal deformation temperature may be lowered. As a result, processability in manufacturing fuel cells by hot pressing, and joining properties with electrodes may be improved.

In Formula (1), l and o are each an integer of 0 to 4; m is an integer of 1 to 4; q is an integer of 2 or greater; n and p indicate a composition ratio of the respective units and are each a number ranging from 0 to 1; n+p=1; and n is not 0. In particular, m is preferably 1, l is preferably 0 or 1, and n is preferably in the range of 0.3 to 1.

A and E are each at least one structure selected from the group consisting of a direct bond, —O—, —S—, —CO—, —SO$_2$—, —SO—, —CONH—, —COO—, —(CF$_2$)$_f$— (wherein f is an integer of 1 to 10), —(CH$_2$)$_h$— (wherein h is an integer of 1 to 10), —CR'$_2$— (wherein R' is an aliphatic hydrocarbon group, an aromatic hydrocarbon group or a halogenated hydrocarbon group), a cyclohexylidene group and a fluorenylidene group. Specific examples of the structures represented by —CR'$_2$— include methyl, ethyl, propyl, isopropyl, butyl, isobutyl, t-butyl, propyl, octyl, decyl, octadecyl, phenyl and trifluoromethyl groups.

Of these, a direct bond, —O—, —CO—, —SO—, —SO$_2$—, —CR'$_2$—, —(CF$_2$)$_f$—, —(CH$_2$)$_h$—, a cyclohexylidene group and a fluorenylidene group are preferred.

Each B is independently an oxygen atom or a sulfur atom, and is preferably an oxygen atom.

D is at least one structure selected from the group consisting of a direct bond, —O—, —S—, —CO—, —SO$_2$—, —SO—, —CONH—, —COO—, —(CF$_2$)$_f$— (wherein f is an integer of 1 to 10), —(CH$_2$)$_h$— (wherein h is an integer of 1 to 10), —CR'$_2$— (wherein R' is an aliphatic hydrocarbon group, an aromatic hydrocarbon group or a halogenated hydrocarbon group), a cyclohexylidene group and a fluorenylidene group. Specific examples of the structures represented by —CR'$_2$— include methyl, ethyl, propyl, isopropyl, butyl, isobutyl, t-butyl, propyl, octyl, decyl, octadecyl, phenyl and trifluoromethyl groups. Of these, a direct bond, —O—, —SO—, —(CH$_2$)$_n$— and —CR"$_2$— (wherein R" is an aliphatic hydrocarbon group or an aromatic hydrocarbon group) are preferred.

X is an atom or a group selected from halogen atoms other than fluorine, —OSO$_2$CH$_3$ and —OSO$_2$CF$_3$. In particular, halogen atoms other than fluorine are preferred, and Cl or Br is more preferred.

R$_1$ to R$_{28}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group.

In a more preferred embodiment, the compound is represented by Formula (3) below:

[Chem. 8]

$$X \left[ \left[ P-O-\bigcirc-D-\bigcirc-D-\bigcirc-O \right]_n (P-O-Q-O)_p \right]_q P-X \quad (3)$$

In Formula (3), X is an atom selected from halogen atoms other than fluorine; D is —O— or —CR"$_2$— (wherein R" is an aliphatic hydrocarbon group or an aromatic hydrocarbon group); P is at least one structure selected from structures represented by Formulae (4-1) to (4-3) below; Q is represented by any of the following formulae; q is an integer of 2 or greater; n and p indicate a composition ratio of the respective units and are each a number ranging from 0 to 1; n+p=1; and n is not 0.

[Chem. 9]

(4-1)

(4-2)

(4-3)

(5-1)

(5-2)

(5-3)

(5-4)

(5-5)

(5-6)

(5-7)

(5-8)

(5-9)

(5-10)

(5-11)

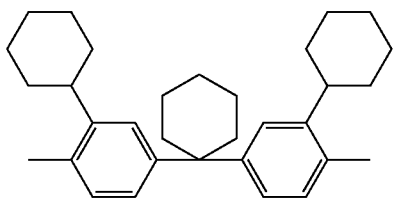

(5-12)

The compounds of Formula (1) may be synthesized for example by the following method.

A bisphenol in which the phenol groups are linked via a divalent atom or organic group or a direct bond, is converted into an alkali metal salt of the bisphenol. To convert into alkaline salt, alkali compounds such as an alkali metal, an alkali metal hydride, an alkali metal hydroxide or an alkali metal carbonate is added to the bisphenols in a polar solvent of high dielectric constant such as N-methyl-2-pyrrolidone, N,N-dimethylacetamide, sulfolane, diphenylsulfone or dimethylsulfoxide. The alkali metal includes lithium, sodium and potassium. The alkali compound is used in slight excess over the hydroxyl groups of the bisphenols, for example 1.1 to 2 times, preferably 1.2 to 1.5 times the equivalent weight of the hydroxyl groups. Here, it is preferable that the reaction is accelerated by using a solvent that forms an azeotropic mixture with water, such as benzene, toluene, xylene, chlorobenzene or anisole.

Thereafter, the alkali metal salt of the bisphenol is reacted with a dihalide compound substituted with a halogen atom such as chlorine and a nitrile group.

Examples of the bisphenols include those having three or more consecutive benzene rings, such as 4,4'-(1,3-phenylenediisopropylidene)bisphenol, 4,4'-(1,4-phenylenediisopropylidene)bisphenol, 1,3-(4-hydroxybenzoyl benzene), 1,4-(4-hydroxybenzoyl benzene), 1,3-bis(4-hydroxyphenoxy)benzene, 1,4-bis(4-hydroxyphenoxy)benzene, 1,4-bis(4-hydroxyphenyl)benzene and 1,3-bis(4-hydroxyphenyl)benzene. Of these, 4,4'-(1,3-phenylenediisopropylidene) bisphenol and 4,4'-(1,4-phenylenediisopropylidene) bisphenol are preferred.

Examples of the bisphenols further include 4,4'-isopropylidenebisphenol, 2,2-bis(4-hydroxyphenyl)-1,1,1,3,3,3-hexafluoropropane, 4,4'-bishydroxybenzophenone, 4,4'-bishydroxydiphenylsulfone, 4,4'-dihydroxydiphenyl ether, 4,4'-dihydroxybiphenyl, bis(4-hydroxyphenyl)methane, resorcinol, hydroquinone, 2,6-dihydroxynaphthalene, 9,9-bis(4-hydroxyphenyl)fluorene, 4,4'-isopropylidene bis(2-phenylphenol) and 4,4'-cyclohexylidene bis(2-cyclohexylphenol).

Examples of the dihalide compounds include 4,4'-dichlorobenzophenone, 4,4'-difluorobenzophenone, 4-chloro-4'-fluorobenzophenone, 2-chloro-4'-fluorobenzophenone, 4,4'-dichlorodiphenylsulfone, 4,4'-difluorodiphenylsulfone, 2,6-dinitrobenzonitrile, 2,5-dinitrobenzonitrile, 2,4-dinitrobenzonitrile, 2,6-dichlorobenzonitrile, 2,5-dichlorobenzonitrile, 2,4-dichlorobenzonitrile, 2,6-difluorobenzonitrile, 2,5-difluorobenzonitrile, 2,4-difluorobenzonitrile and 2-chloro-6-fluorobenzonitrile.

The dihalide compound may be added in an amount 1.0001 to 3 times, preferably 1.001 to 2 times the molar amount of the bisphenol. To make sure that the obtainable compound will be terminated with a chlorine atom at both ends, the reaction product may be further reacted by adding an excess of a dichloro compound. In the case where a difluoro compound or a dinitro compound is used, a dichloro compound will be added at a later stage of the reaction to make sure that the obtainable compound will be terminated with a chlorine atom at both ends.

In these reactions, the reaction temperature is in the range of 60 to 300° C., preferably 80 to 250° C., and the reaction time ranges from 15 minutes to 100 hours, preferably from 1 to 24 hours.

The oligomer or polymer obtained may be purified by general polymer purification methods such as dissolution and precipitation. The molecular weight may be adjusted by controlling the molar ratio in the reaction between the excess aromatic dichloride and the bisphenol. Because the aromatic dichloride is in excess, the oligomer or polymer obtained has molecular ends terminated with aromatic chloride.

Specific examples of the structures of the compounds obtained by the above method include:

[Chem. 10]

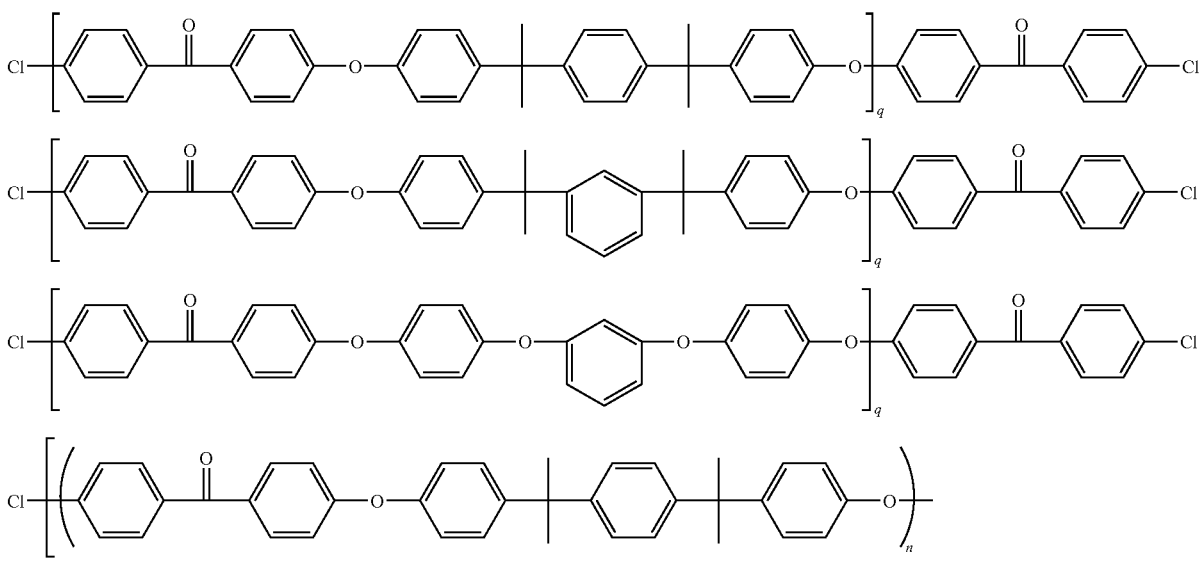

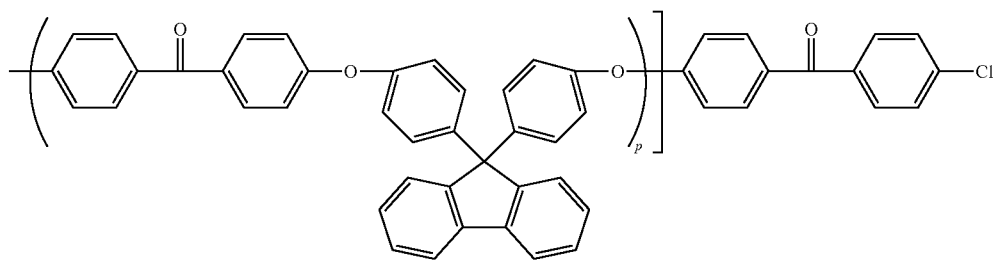
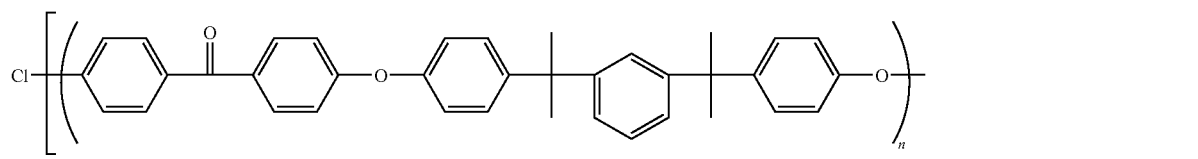
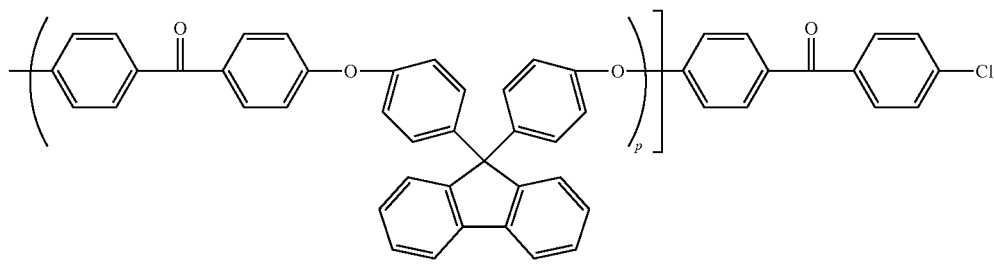
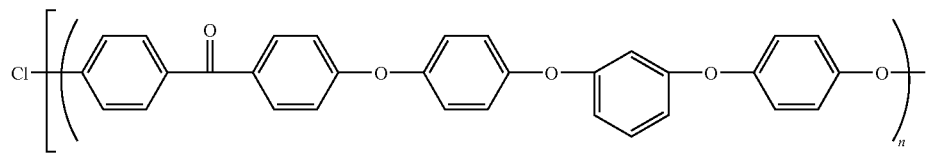
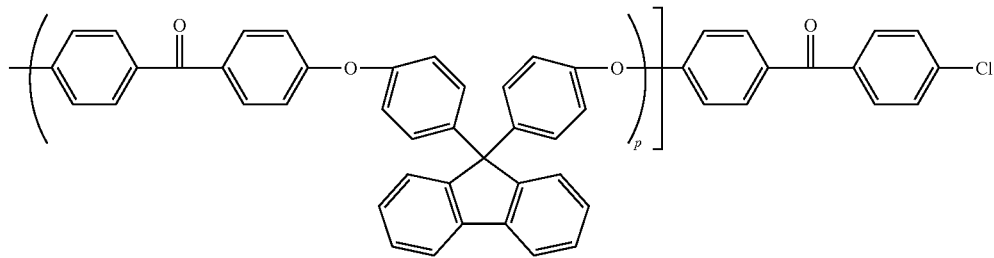
[Chem. 11]
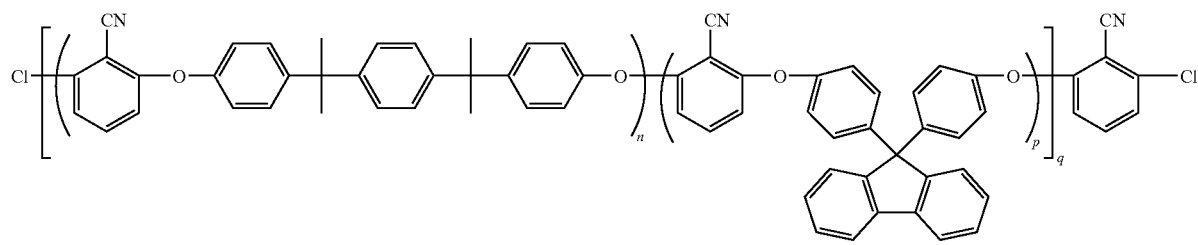
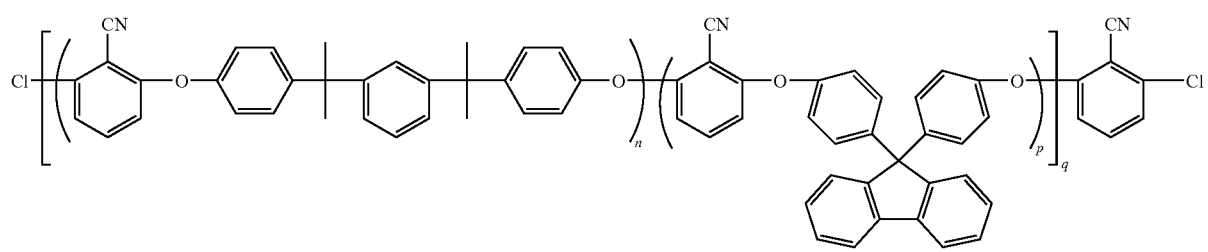

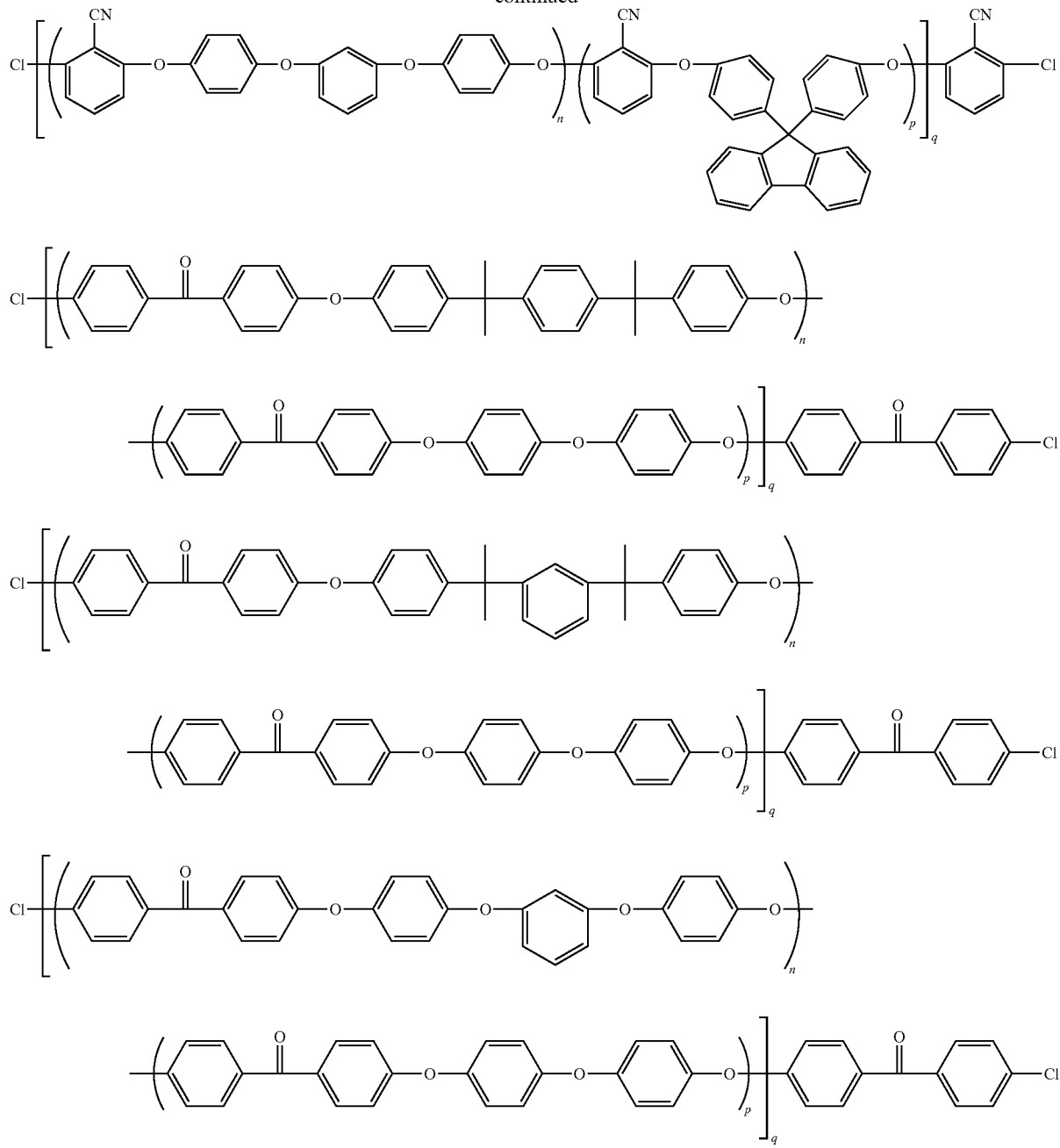

Of these compounds, those synthesized from 4,4'-(1,3-phenylenediisopropylidene)bisphenol and 4,4'-(1,4-phenylenediisopropylidene)bisphenol are preferred.

The glass transition temperature of the polymer may be adjusted by changing the composition ratio of the units indicated by "n" and "p". From the viewpoint of polymer processability, compounds in which n=0.3 to 1 are useful. Such compounds have a flexible main chain skeleton and thus a low thermal deformation temperature. Therefore, when a polymer derived from the above compound is used for fuel cell, processability in manufacturing fuel cells by hot pressing, and joining properties between with electrodes are improved. Further, such aromatic compounds provide hydrophobic structural units. Thereby, if the polyarylene polymers which are derived from the above compound contains the sulfonic acid groups in a high concentration, the polymers can give polymer electrolytes and proton conductive membranes that have high methanol resistance, good processability and high proton conductivity.

[Polyarylene Copolymers]

The polyarylene polymers according to the present invention may be homopolymers consisting of a structural unit represented by Formula (1') below (hereinafter, the "structural unit (1')), or may be copolymers of the structural unit (1') and another structural unit. In both cases, the weight average molecular weight of the polymers measured by gel permeation chromatography relative to polystyrene standards (hereinafter, simply the "weight average molecular weight") is 10000 to 1000000, preferably 20000 to 800000.

[Chem. 12]

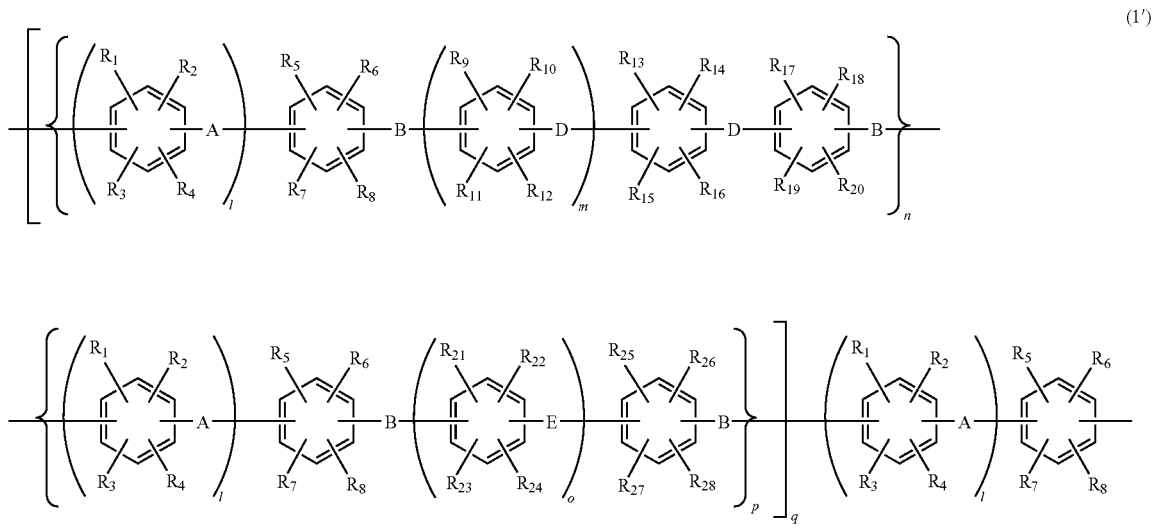

(1')

In Formula (1'), $R_1$ to $R_{28}$, A, B, D, E, l, m, n, o, p and q are the same as $R_1$ to $R_{28}$, A, B, D, E, l, m, n, o, p and q in Formula (1).

The polyarylene copolymers may contain structural units other than the structural unit (1') as required. Preferred examples of such structural units include those represented by Formula (A) below (hereinafter, also the "structural units (A)"). The copolymers including the structural units (A) are suitable as proton conductive solid polymer electrolytes and proton conductive membranes, in particular proton conductive membranes for direct methanol fuel cells.

The polyarylene copolymers including the structural units (A) are also referred to as the "sulfonated polyarylenes" in the specification.

The sulfonated polyarylenes used in the invention will be described in detail. The sulfonated polyarylenes contain a structural unit with a sulfonic acid group represented by Formula (A) below (sulfonic acid unit) and a hydrophobic structural unit represented by Formula (1') above (structural unit (1')), and are represented by Formula (C) below.

<Sulfonic Acid Units>

[Chem. 13]

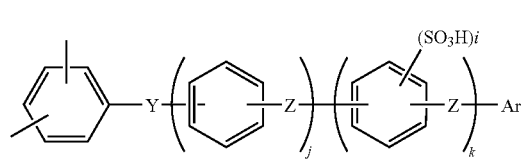

(A)

In Formula (A), Y is at least one structure selected from —CO—, —SO$_2$—, —SO—, —CONH—, —COO—, —(CF$_2$)$_l$— (wherein l is an integer of 1 to 10) and —C(CF$_3$)$_2$—. Of these, —CO— and —SO$_2$— are preferable.

Z independently represents at least one structure selected from the group consisting of a direct bond, —(CH$_2$)$_l$— (wherein l is an integer of 1 to 10), —C(CH$_3$)$_2$—, —O— and —S—. Of these, a direct bond and —O— are preferred.

Ar is an aromatic group with a substituent represented by —SO$_3$H, —O(CH$_2$)$_p$SO$_3$H or —O(CF$_2$)$_p$SO$_3$H (wherein p is an integer of 1 to 12).

Examples of the aromatic groups include phenyl, naphthyl, anthryl and phenanthryl groups, with phenyl and naphthyl groups being preferable. There should be at least one substituent represented by —SO$_3$H, —O(CH$_2$)$_p$SO$_3$H or —O(CF$_2$)$_p$SO$_3$H (wherein p is an integer of 1 to 12). When the aromatic group is a naphthyl group, it preferably has two or more such substituents.

The letter j is an integer of 0 to 10, preferably 0 to 2; k is an integer of 0 to 10, preferably 0 to 2; and i is an integer of 1 to 4.

Preferred combinations of j, k, Y, Z and Ar are:

(1) j=0, k=0, Y is —CO— and Ar is a phenyl group having a substituent —SO$_3$H;

(2) j=1, k=0, Y is —CO—, Z is —O— and Ar is a phenyl group having a substituent —SO$_3$H;

(3) j=1, k=1, i=1, Y is —CO—, Z is —O— and Ar is a phenyl group having a substituent —SO$_3$H;

(4) j=1, k=0, Y is —CO—, Z is —O— and Ar is a naphthyl group having two substituents —SO$_3$H; and (5) j=1, k=0, Y is —CO—, Z is —O— and Ar is a phenyl group having a substituent —O(CH$_2$)$_4$SO$_3$H.

<Polymer Structure>

[Chem. 14]

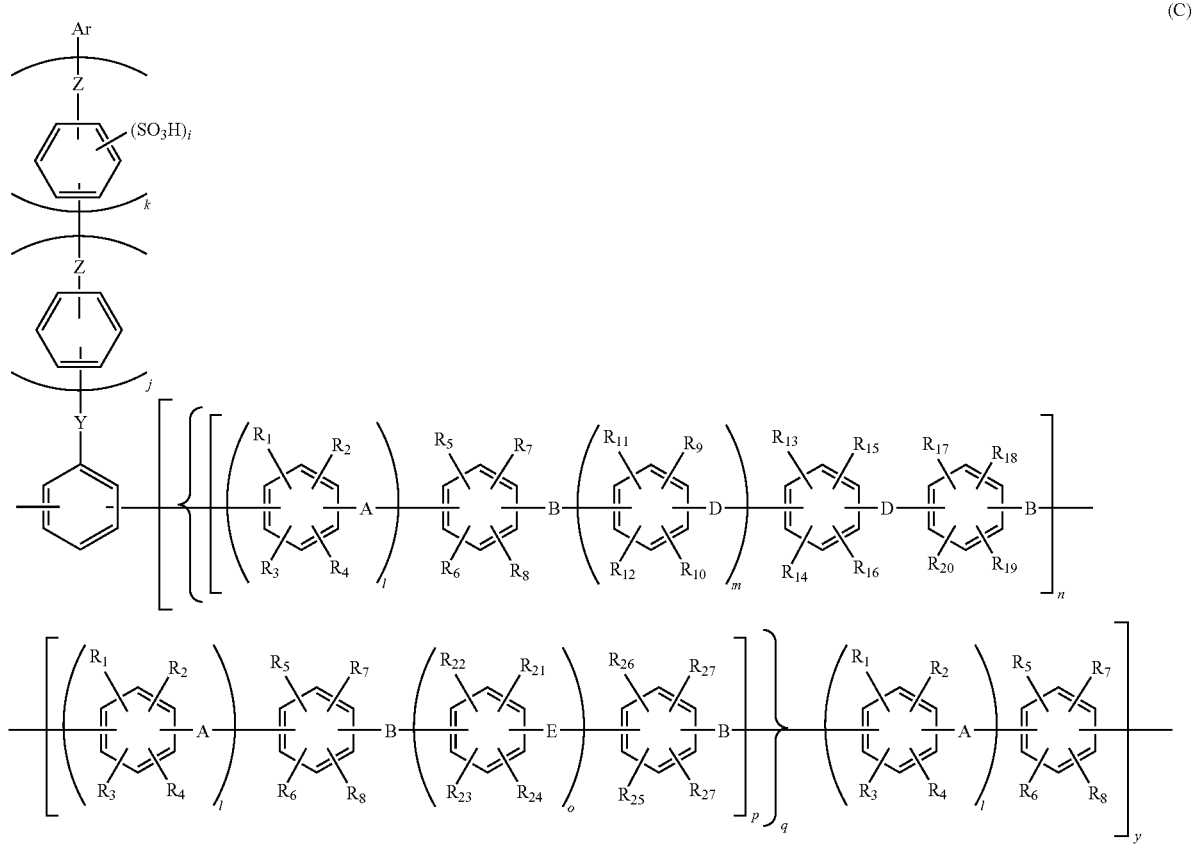

(C)

In Formula (C), A, B, D, E, Y, Z, Ar, i, k, j, l, m, n, o, p, q and $R_1$ to $R_{28}$ are the same as A, B, D, E, Y, Z, Ar, i, k, j, l, m, n, o, p, q and $R_1$ to $R_{28}$ in Formulae (1) and (A), and x and y indicate a molar ratio relative to x+y=100 mol %.

The sulfonated polyarylenes contain the structural unit of Formula (1 ') i.e. the unit x, at 0.5 to 99.999 mol %, preferably 10 to 99.9 mol %, and the structural unit of Formula (B), i.e. unit y, at 99.5 to 0.001 mol %, preferably 90 to 0.1 mol %.

<Polymer Production>

The sulfonated polyarylenes may be produced for example by the following three methods A, B and C (Method A)

This method is described in JP-A-2004-137444. A monomer with a sulfonate group capable of forming a structural unit of Formula (A) is copolymerized with a monomer or oligomer capable of forming a structural unit represented by Formula (B) to produce a polyarylene having a sulfonate group. The polyarylene is de-esterified to convert the sulfonate group into a sulfonic acid group.

(Method B)

This method is described in JP-A-2001-342241. A monomer which has a skeleton represented by Formula (A) and does not have a sulfonic acid group or a sulfonate group is copolymerized with a monomer or oligomer capable of forming a structural unit represented by Formula (B). The resultant polymer is sulfonated with a sulfonating agent.

(Method C)

When Ar in Formula (A) is an aromatic group having a substituent represented by —O(CH$_2$)$_p$SO$_3$H or —O(CF$_2$)$_p$SO$_3$H, a method described in JP-A-2005-60625 may be used. A monomer of a precursor capable of forming a structural unit of Formula (A) is copolymerized with a monomer or oligomer capable of forming a structural unit represented by Formula (B). Next, an alkylsulfonic acid or a fluorine-substituted alkylsulfonic acid is introduced.

Examples of the monomers with a sulfonate group capable of forming a structural unit of Formula (A) that may be used in Method (A) include sulfonates as described in JP-A-2004-137444, JP-A-2004-346163 and JP-A-2004-346163.

Examples of the monomers used in Method (B) which can form a structural unit represented by Formula (A) and do not have a sulfonic acid group or a sulfonate group include dihalides described in JP-A-2001-342241 and JP-A-2002-293889.

Examples of the monomers of precursors capable of forming a structural unit represented by Formula (A) that may be used in Method (C) include dihalides described in JP-A-2005-36125.

To produce the sulfonated polyarylene, a monomer capable of forming a structural unit of Formula (A) is first copolymerized with a monomer or oligomer capable of forming a structural unit of Formula (B) to obtain a precursor polyarylene. This copolymerization is carried out in the presence of a catalyst. The catalyst used herein is a catalyst system containing a transition metal compound. The catalyst system essentially contains (1) a transition metal salt and a compound that functions as a ligand (also referred to as the "ligand component"), or a transition metal complex (inclusive of copper salt) to which a ligand is coordinated, and (2) a reducing agent. A "salt" may be added to increase the polymerization rate.

Specific examples of these catalyst components, amounts of the materials, and polymerization conditions such as reaction solvents, concentrations, temperature and time include compounds described in JP-A-2001-342241.

The sulfonated polyarylene may be obtained by converting the precursor polyarylene into a polyarylene having a sulfonic acid group. For the conversion, the following three methods may be used.

(Method A)

The precursor polyarylene with a sulfonate group is de-esterified by a method described in JP-A-2004-137444.

(Method B)

The precursor polyarylene is sulfonated by a method described in JP-A-2001-342241.

(Method C)

An alkylsulfonic acid group is introduced into the precursor polyarylene by a method described in JP-A-2005-60625.

The sulfonated polyarylene of Formula (C) synthesized as described above generally has an ion exchange capacity in the range of 0.3 to 5 meq/g, preferably 0.5 to 3 meq/g, more preferably 0.8 to 2.8 meq/g. If the ion exchange capacity is less than 0.3 meq/g, proton conductivity is low and power generation performance is poor. If the capacity exceeds 5 meq/g, water resistance may be drastically deteriorated.

The ion exchange capacity may be controlled for example by changing the types, amounts and combination of the monomer of a precursor for a structural unit of Formula (1) and the monomer or oligomer for a structural unit of Formula (A).

The weight average molecular weight of the sulfonated polyarylene determined by gel permeation chromatography (GPC) relative to polystyrene standards is in the range of 10000 to 1000000, preferably 20000 to 800000.

[Solid Polymer Electrolytes]

The solid polymer electrolyte according to the invention comprises the above-described sulfonated polyarylene polymer. It may further contain an antioxidant such as a phenolic hydroxyl group-containing compound, an amine compound, an organophosphorus compound or an organosulfur compound, without adversely affecting the proton conductivity.

The solid polymer electrolyte may be used in various forms including particles, fibers and membranes, as required depending on application. For example, membranes (generally called proton conductive membranes) are desirable in the case of electrochemical devices such as fuel cells and water hydrolysis devices.

[Proton Conductive Membranes]

The proton conductive membrane of the invention is made from the solid polymer electrolyte comprising the sulfonated polyarylene polymer. Production of the proton conductive membranes may involve, together with the solid polymer electrolyte, inorganic acids such as sulfuric acid and phosphoric acid, organic acids including carboxylic acids, an appropriate amount of water, and the like.

In the invention, the proton conductive membrane may be produced by a casting method in which the sulfonated polyarylene polymer dissolved in a solvent is flow-cast over a substrate to form a film. The substrate used herein is not particularly limited and may be selected from those substrates commonly used in the solution casting methods. Examples thereof include plastic substrates and metal substrates. Preferably, thermoplastic resin substrates such as polyethyleneterephthalate (PET) films are used.

The solvents to dissolve the sulfonated polyarylene polymer include aprotic polar solvents such as N-methyl-2-pyrrolidone, N,N-dimethylformamide, γ-butyrolactone, N,N-dimethylacetamide, dimethylsulfoxide, dimethylurea and dimethylimidazolidinone. In view of solvent properties (property capable dissolving the solutes) and solution viscosity, N-methyl-2-pyrrolidone (also "NMP") is preferable. The aprotic polar solvents may be used singly, or two or more kinds may be used in combination.

The solvent for dissolving the sulfonated polyarylene polymer may be a mixed solvent of the above aprotic polar solvent and an alcohol. Exemplary alcohols include methanol, ethanol, propyl alcohol, iso-propyl alcohol, sec-butyl alcohol and tert-butyl alcohol. In particular, methanol is preferable because it ensures an appropriately low solution viscosity over a wide range of proportions of the polymer. These alcohols may be used singly, or two or more kinds may be used in combination.

The above mixed solvent may contain the aprotic polar solvent in an amount of 95 to 25 wt %, preferably 90 to 25 wt %, and the alcohol in an amount of 5 to 75 wt %, preferably 10 to 75 wt % (the total is 100 wt %). This proportion of the alcohol content leads to an appropriately low solution viscosity.

Although the concentration of the sulfonated polyarylene polymer in the solution depends on the molecular weight of the sulfonated polyarylene polymer, it is generally from 5 to 40 wt %, preferably from 7 to 25 wt %. The concentration less than 5 wt % causes difficulties in producing the membranes in large thickness and results in easy occurrence of pinholes. If the concentration exceeds 40 wt %, the solution viscosity becomes so high that the film production will be difficult and further that the obtainable films may have low surface smoothness.

The solution viscosity may vary depending on the molecular weight or the concentration of the sulfonated polyarylene polymer. Generally, it ranges from 2,000 to 100,000 mPa·s, preferably from 3,000 to 50,000 mPa·s. If the viscosity is less than 2,000 mPa·s, the solution will have too high a fluidity and may spill out of the substrate during the membrane production. The viscosity over 100,000 mPa·s is so high that the solution cannot be extruded through a die and the flow-casting for the film production may be difficult.

The wet film obtained as described above may be soaked into water to substitute the organic solvent in the film with water. This treatment reduces the amount of the residual solvent in the obtainable proton conductive membrane.

Prior to the soaking into water, the wet film may be pre-dried. The predrying may be performed by holding the wet film at 50 to 150° C. for 0.1 to 10 hours.

Soaking the wet films in water may be carried out batch-wise with respect to each film, or may be a continuous process wherein the films, which may be in the original form of laminates on the substrate film (e.g. PET film) as produced or which may be released from the substrate, are soaked in water and then wound sequentially.

In the batchwise soaking, the films are suitably framed or fixed by similar means to prevent wrinkles from forming on the surface of the treated films.

The soaking may be suitably made so that the wet films will contact water that is at least 10 parts by weight, preferably at least 30 parts by weight based on 1 part by weight of the wet films. This contact ratio is suitably kept as large as possible to minimize the amount of the solvent remaining in the obtainable proton conductive membrane. In order to reduce the residual solvent amount in the proton conductive membrane, it is also effective to keep the concentration of the organic solvent in water at or below a certain level by renewing the water used in the soaking or by overflowing water. The in-plane distribution of the organic solvent within the proton conductive membrane may be uniformed by homogenizing the organic solvent concentration in water by stirring or the like.

When the wet film is soaked in water, the water temperature is preferably from 5 to 80° C. Although the substitution between the organic solvent and water takes place at a higher rate as the temperature rises, the water absorption of the film will also increase at higher temperatures. Consequently, the proton conductive membrane may have a rough surface after dried. In general, the water temperature is suitably 10 to 60° C. from the viewpoints of substitution rate and easy handling.

The soaking time varies depending on the initial amount of the residual solvent, the contact ratio and the treatment temperature. Generally, the soaking time ranges from 10 minutes to 240 hours, preferably from 30 minutes to 100 hours.

By drying the water-soaked film, a proton conductive membrane is obtained which has a reduced amount of the residual solvent. The amount of the residual solvent in the proton conductive membrane is generally not more than 5 wt %.

Controlling the soaking conditions enables reduction of the residual solvent down to 1 wt % or less of the proton conductive membrane. For example, this is possible when the wet film is soaked in water that is at least 50 parts by weight based on 1 part by weight of the wet film, at a water temperature of 10 to 60° C. for 10 minutes to 10 hours.

After the wet film is soaked in water as described above, the film is dried at 30 to 100° C., preferably 50 to 80° C., for 10 to 180 minutes, preferably 15 to 60 minutes. Subsequently, it is vacuum dried at 50 to 150° C. and preferably at 500 to 0.1 mm Hg for 0.5 to 24 hours. The proton conductive membrane according to the invention may be thus obtained.

The proton conductive membranes obtained by the above method range in dry thickness from 10 to 100 µm, preferably from 20 to 80 µm.

In an embodiment of the production of the proton conductive membranes, the polyarylene polymer with a sulfonate group may be formed into a film by the above method without undergoing hydrolysis, and may be thereafter hydrolyzed by the above method to produce a proton conductive membrane comprising the sulfonated polyarylene polymer.

The proton conductive membrane may contain an anti-aging agent, preferably a hindered phenol compound with a molecular weight of not less than 500. Such anti-aging agents provide longer durability of the proton conductive membrane.

The hindered phenol compounds with a molecular weight of 500 or more employable in the invention include triethylene glycol-bis[3-(3-t-butyl-5-methyl-4-hydroxyphenyl)propionate] (trade name: IRGANOX 245), 1,6-hexanediol-bis [3-(3,5-di-t-butyl-4-hydroxyphenyl)propionate] (trade name: IRGANOX 259), 2,4-bis-(n-octylthio)-6-(4-hydroxy-3,5-di-t-butylanilino)-3,5-triadine (trade name: IRGANOX 565), pentaerythrityl-tetrakis[3-(3,5-di-t-butyl-4-hydroxyphenyl)propionate] (trade name: IRGANOX 1010), 2,2-thio-diethylene bis[3-(3,5-di-t-butyl-4-hydroxyphenyl)propionate] (trade name: IRGANOX 1035), octadecyl-3-(3,5-di-t-butyl-4-hydroxyphenyl)propionate) (trade name: IRGANOX 1076), N,N-hexamethylene bis (3,5-di-t-butyl-4-hydroxy-hydrocinnamide) (trade name: IRGANOX 1098), 1,3,5-trimethyl-2,4,6-tris(3,5-di-t-butyl-4-hydroxybenzyl) benzene (trade name: IRGANOX 1330), tris-(3,5-di-t-butyl-4-hydroxybenzyl)-isocyanurate (trade name: IRGANOX 3114) and 3,9-bis[2-[3-(3-t-butyl-4-hydroxy-5-methylphenyl)propionyloxy]-1,1-dimethylethyl]-2,4,8,10-tetraoxaspiro[5.5]undecane (trade name: Sumilizer GA-80).

The hindered phenol compound with 500 or more molecular weight may be preferably used in an amount of 0.01 to 10 parts by weight based on 100 parts by weight of the sulfonated polyarylene polymer.

The proton conductive membranes of the invention may be suitably used as electrolytes for primary and secondary batteries, solid polymer electrolytes for fuel cells, and other proton conductive membranes for display elements, sensors, signaling media, solid condensers and ion exchange membranes.

Further, the proton conductive membranes of the invention are suited for use as solid polymer electrolytes or proton conductive membranes for direct methanol fuel cells.

EXAMPLES

The present invention will be described based on Examples below without limiting the scope of the invention. Properties were measured by the following methods.

(Molecular Weight)

The number average molecular weight (Mn) of the hydrophobic unit before sulfonation was measured by GPC using tetrahydrofuran (THF) as a solvent relative to polystyrene standards. The weight average molecular weight (Mw) of the sulfonated polymer was measured by GPC relative to polystyrene standards using an eluting solution consisting of N-methyl-2-pyrrolidone (NMP) mixed with lithium bromide and phosphoric acid.

(Ion Exchange Capacity)

The sulfonated polymer was washed with water until the pH of the washings became 4 to 6, and free residual acids were removed. The polymer was sufficiently washed with water and then dried. A predetermined amount of the polymer was weighed out and dissolved in a THF/water mixed solvent. The solution mixed with phenolphthalein as an indicator was titrated with a NaOH standard solution to obtain a point of neutralization, from which the ion exchange capacity was determined.

(Glass Transition Temperature)

The glass transition temperature of the sulfonated polymer was determined with a dynamic viscoelastometer.

(Aqueous Methanol Solution Soaking Test)

The conductive membrane was soaked in a 64 wt % aqueous methanol solution at 60° C. for 6 hours. The area was measured before and after the soaking to obtain an area percentage change (%).

Area percentage change (%)=(Area after soaking/area before soaking)×100

(Methanol Permeability)

Methanol permeability was measured by pervaporation method. The membrane was set in a predetermined cell and a 30 wt % aqueous methanol solution was supplied on the upper surface. The solution was suctioned from the back surface, and the liquid that penetrated the membrane was trapped with liquid nitrogen. The quantity of methanol permeation was calculated from the following equation:

Methanol permeation quantity (g/m$^2$/h)=[weight of penetrating liquid (g)/collecting time (h)/sample area (m$^2$)]×methanol concentration of penetrating liquid

[Chem. 15]

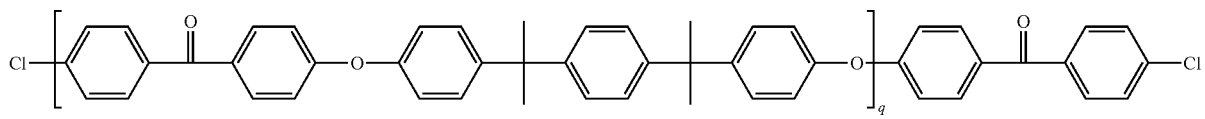

(I)

(Measurement of Membrane Resistance)

The membrane was sandwiched between conductive carbon plates through 1 mol/L sulfuric acid, and the alternating current resistance between the carbon plates was measured at room temperature. The membrane resistance was determined from the following equation:

Membrane resistance (Ω·cm$^2$)=resistance (Ω) between carbon plates through membrane−blank (Ω)× contact area (cm$^2$)

(Electrode Joining Properties)

Commercially available carbon electrodes and the membrane were pressed at 75 kg/cm$^2$ and 140° C. for 5 minutes. The assembly was soaked in a 10 wt % aqueous methanol solution for 24 hours, and the bonding of the electrodes was visually inspected.

AA: No separation, CC: Separation

Example 1

Synthesis of Hydrophobic Unit

A 1-liter separable three-necked flask equipped with a stirring blade, a thermometer, a nitrogen inlet tube, a Dean-Stark tube and a condenser tube was charged with 60.3 g (240 mmol) of 4,4'-dichlorobenzophenone, 69.3 g (200 mmol) of 4,4'-(1,4-phenylenediisopropylidene)bisphenol (Bis-P) and 35.9 g (260 mmol) of potassium carbonate. Further, 370 mL of sulfolane and 190 mL of toluene were added. The mixture was heated at 150° C. under reflux in a nitrogen atmosphere. Water resulting from the reaction was formed into an azeotropic mixture with toluene and was removed through the Dean-Stark tube. Water ceased to occur after 3 hours, and toluene was removed from the reaction system. The reaction liquid was stirred at 180° C. for 7 hours, and 20.1 g (80 mmol) of 4,4'-dichlorobenzophenone was added, followed by stirring for 3 hours. The reaction liquid was left to cool, and inorganic matters insoluble in the reaction solution were removed by filtration with filter aid Celite. The filtrate was poured into 2.0 L of methanol to precipitate the reaction product. The precipitate was filtered, washed with a small amount of methanol, and vacuum dried. The dried product was redissolved in 200 mL of tetrahydrofuran. The solution was poured into 2.0 L of methanol to reprecipitate the product. The precipitate was filtered and vacuum dried to give 103 g of an objective compound (92% yield). The number average molecular weight and weight average molecular weight by GPC relative to polystyrene standards were 4500 and 6800, respectively. The compound was identified to be an oligomer represented by Formula (1):

Example 2

Synthesis of Sulfonated Polymer

A 1-liter three-necked flask equipped with a stirrer, a thermometer and a nitrogen inlet tube was charged with 53.3 g (133 mmol) of neopentyl 3-(2,5-dichlorobenzoyl)benzenesulfonate, 74.7 g (16.6 mmol) of the hydrophobic unit from Example 1 with 4500 number average molecular weight, 2.94 g (5.0 mmol) of bis(triphenylphosphine)nickel dichloride, 0.67 g (5.0 mmol) of sodium iodide, 15.7 g (60 mmol) of triphenylphosphine and 23.5 g (360 mmol) of zinc. The flask was then purged with dry nitrogen. Subsequently, 320 mL of N,N-dimethylacetamide (DMAc) was added to the flask, and stirring was performed for 3 hours while maintaining the reaction temperature at 80° C. The reaction liquid was then diluted with 540 mL of DMAc, and insolubles were filtered.

The resultant solution was placed in a 2-liter three-necked flask equipped with a stirrer, a thermometer and a nitrogen inlet tube, and was heated to 115° C. with stirring. Subsequently, 23.2 g (266 mmol) of lithium bromide was added, followed by stirring for 7 hours. The resultant solution was poured into 3.5 L of acetone to precipitate the product. The product was sequentially washed with 1N hydrochloric acid and pure water in this order, and was dried to give 92 g of an objective polymer. The polymer had a weight average molecular weight (Mw) of 85000. The polymer was identified to be represented by Formula (II):

[Chem. 16]

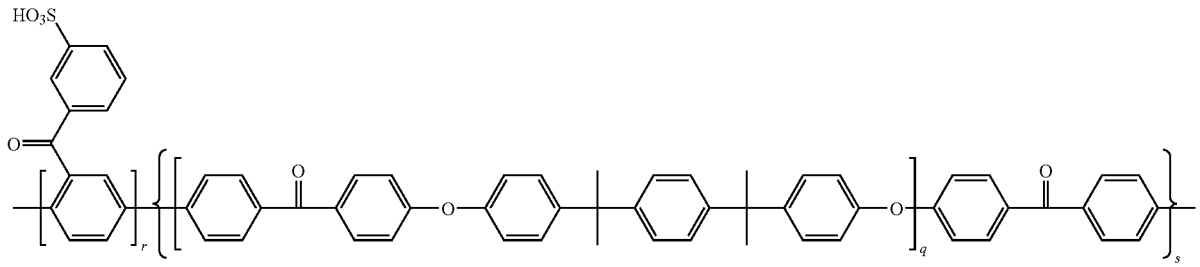

(II)

A 10 wt % N-methylpyrrolidone (NMP) solution of the sulfonated polymer was cast over a glass plate to give a film with a thickness of 40 µm.

Example 3

Synthesis of Hydrophobic Unit

A 1-liter separable three-necked flask equipped with a stirring blade, a thermometer, a nitrogen inlet tube, a Dean-Stark tube and a condenser tube was charged with 52.4 g (240 mmol) of 4,4'-difluorobenzophenone, 14.1 g (60.0 mmol) of 4-chloro-4'-fluorobenzophenone, 70.2 g (203 mmol) of 4,4'-(1,3-phenylenediisopropylidene)bisphenol (Bis-M), 23.7 g (67.5 mmol) of bis(4-hydroxyphenyl)fluorene and 48.5 g (351 mmol) of potassium carbonate. Further, 430 mL of DMAc and 220 mL of toluene were added. The mixture was heated at 150° C. under reflux in a nitrogen atmosphere. Water resulting from the reaction was formed into an azeotropic mixture with toluene and was removed through the Dean-Stark tube. Water ceased to occur after 3 hours, and toluene was removed from the reaction system. The reaction liquid was stirred at 160° C. for 7 hours, and 7.0 g (20.0 mmol) of 4-chloro-4'-fluorobenzophenone was added, followed by stirring for 3 hours.

The reaction liquid was left to cool, and inorganic matters insoluble in the reaction solution were removed by filtration with filter aid Celite. The filtrate was poured into 2.0 L of methanol to precipitate the reaction product. The precipitate was filtered, washed with a small amount of methanol, and vacuum dried. The dried product was redissolved in 200 mL of tetrahydrofuran. The solution was poured into 2.0 L of methanol to reprecipitate the product. The precipitate was filtered and vacuum dried to give 110 g of an objective compound (80% yield). The number average molecular weight and weight average molecular weight by GPC relative to polystyrene standards were 6000 and 8300, respectively. The compound was identified to be an oligomer represented by Formula (III):

[Chem. 17]

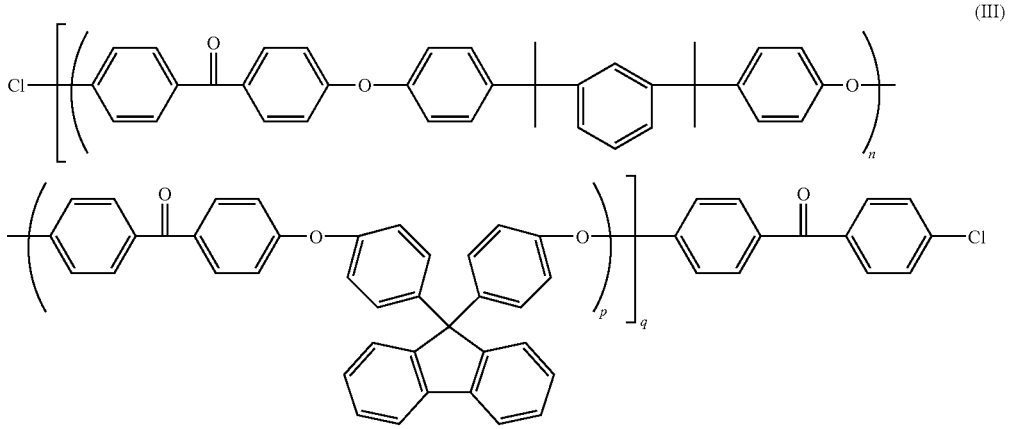

(III)

The composition ratio of n and p was found to be n=0.75 and p=0.25.

Example 4

Synthesis of Sulfonated Polymer

A 1-liter three-necked flask equipped with a stirrer, a thermometer and a nitrogen inlet tube was charged with 56.1 g (140 mmol) of neopentyl 3-(2,5-dichlorobenzoyl)benzenesulfonate, 61.1 g (10.2 mmol) of the hydrophobic unit from Example 3 with Mn 6000, 2.94 g (5.0 mmol) of bis(triphenylphosphine)nickel dichloride, 0.67 g (5.0 mmol) of sodium iodide, 15.7 g (60 mmol) of triphenylphosphine and 23.5 g (360 mmol) of zinc. The flask was then purged with dry nitrogen. Subsequently, 290 mL of N,N-dimethylacetamide (DMAc) was added to the flask, and stirring was performed for 3 hours while maintaining the reaction temperature at 80° C. The reaction liquid was then diluted with 490 mL of DMAc, and insolubles were filtered.

The resultant solution was placed in a 2-liter three-necked flask equipped with a stirrer, a thermometer and a nitrogen inlet tube, and was heated to 115° C. with stirring. Subsequently, 24.3 g (280 mmol) of lithium bromide was added, followed by stirring for 7 hours. The resultant solution was poured into 3.0 L of acetone to precipitate the product. The product was sequentially washed with 1N hydrochloric acid and pure water in this order, and was dried to give 97 g of an objective polymer. The polymer had a weight average molecular weight (Mw) of 105000. The polymer was identified to be represented by Formula (IV):

1,3-bis(4-hydroxyphenoxy)benzene, 45.6 g (130 mmol) of 9,9-bis(4-hydroxyphenyl)fluorene and 46.7 g (338 mmol) of potassium carbonate. Further, 370 mL of sulfolane and 190 mL of toluene were added. The mixture was heated at 150° C. under reflux in a nitrogen atmosphere. Water resulting from the reaction was formed into an azeotropic mixture with toluene and was removed through the Dean-Stark tube. Water ceased to occur after 3 hours, and toluene was removed from the reaction system. The reaction liquid was stirred at 180° C. for 7 hours, and 6.88 g (40 mmol) of 2,6-dichlorobenzonitrile was added, followed by stirring for 3 hours.

The reaction liquid was left to cool, and inorganic matters insoluble in the reaction solution were removed by filtration with filter aid Celite. The filtrate was poured into 2.0 L of

[Chem. 18]

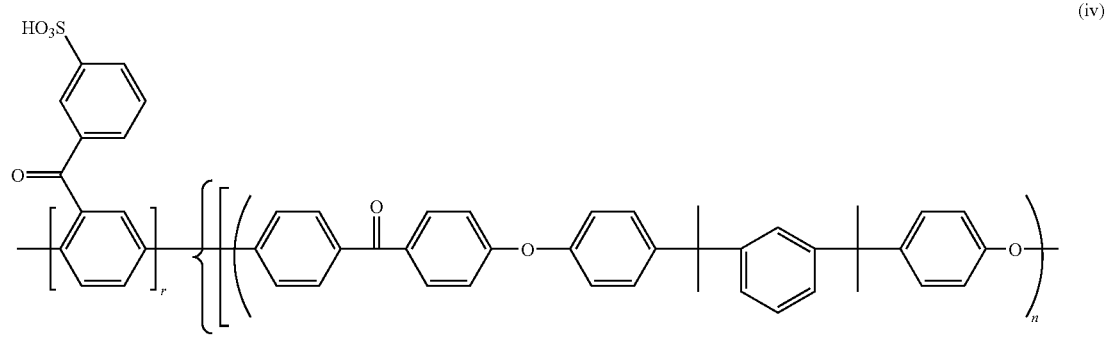

(iv)

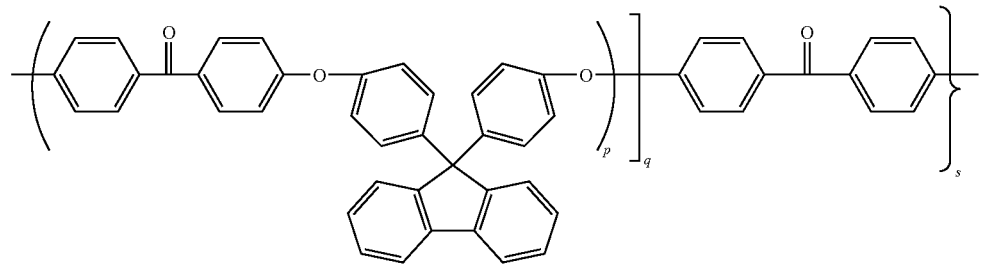

A 10 wt % N-methylpyrrolidone (NMP) solution of the sulfonated polymer was cast over a glass plate to give a film with a thickness of 40 μm.

Example 5

Synthesis of Hydrophobic Unit

A 1-liter separable three-necked flask equipped with a stirring blade, a thermometer, a nitrogen inlet tube, a Dean-Stark tube and a condenser tube was charged with 48.2 g (280 mmol) of 2,6-dichlorobenzonitrile, 38.3 g (130 mmol) of methanol to precipitate the reaction product. The precipitate was filtered, washed with a small amount of methanol, and vacuum dried. The dried product was redissolved in 200 mL of tetrahydrofuran. The solution was poured into 2.0 L of methanol to reprecipitate the product. The precipitate was filtered and vacuum dried to give 106 g of an objective compound (91% yield). The number average molecular weight and weight average molecular weight by GPC relative to polystyrene standards were 8100 and 9500, respectively. The compound was identified to be an oligomer represented by Formula (V):

[Chem. 19]

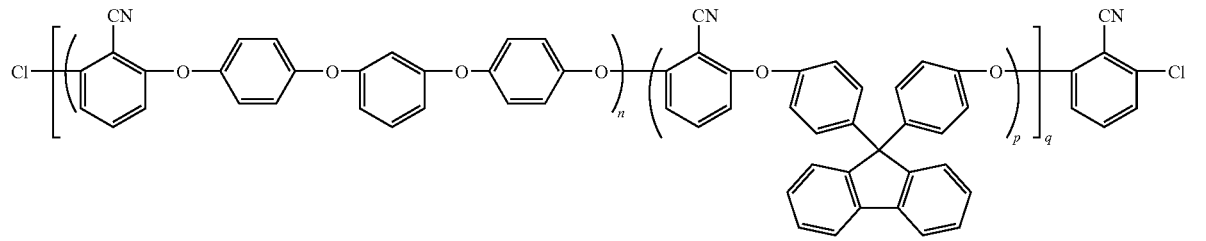

(V)

The composition ratio of n and p was found to be n=0.50 and p=0.50.

Example 6

Synthesis of Sulfonated Polymer

A 1-liter three-necked flask equipped with a stirrer, a thermometer and a nitrogen inlet tube was charged with 56.8 g (141 mmol) of neopentyl 3-(2,5-dichlorobenzoyl)benzenesulfonate, 69.5 g (8.6 mmol) of the hydrophobic unit from Example 5 with Mn 8100, 2.94 g (5.0 mmol) of bis(triphenylphosphine)nickel dichloride, 0.67 g (5.0 mmol) of sodium iodide, 15.7 g (60 mmol) of triphenylphosphine and 23.5 g (360 mmol) of zinc. The flask was then purged with dry nitrogen. Subsequently, 320 mL of N,N-dimethylacetamide (DMAc) was added to the flask, and stirring was performed for 3 hours while maintaining the reaction temperature at 80° C. The reaction liquid was then diluted with 530 mL of DMAc, and insolubles were filtered.

The resultant solution was placed in a 2-liter three-necked flask equipped with a stirrer, a thermometer and a nitrogen inlet tube, and was heated to 115° C. with stirring. Subsequently, 24.6 g (282 mmol) of lithium bromide was added, followed by stirring for 7 hours. The resultant solution was poured into 3.4 L of acetone to precipitate the product. The product was sequentially washed with 1N hydrochloric acid and pure water in this order, and was dried to give 103 g of an objective polymer. The polymer had a weight average molecular weight (Mw) of 97000. The polymer was identified to be represented by Formula (VI):

A 10 wt % N-methylpyrrolidone (NMP) solution of the sulfonated polymer was cast over a glass plate to give a film with a thickness of 40 μm.

Example 7

Synthesis of Hydrophobic Unit

A 1-liter separable three-necked flask equipped with a stirring blade, a thermometer, a nitrogen inlet tube, a Dean-Stark tube and a condenser tube was charged with 45.2 g (180 mmol) of 4,4'-dichlorobenzophenone, 33.3 g (96.0 mmol) of 4,4'-(1,4-phenylenediisopropylidene)bisphenol (Bis-P), 11.9 g (64.0 mmol) of 4,4'-biphenol and 28.7 g (208 mmol) of potassium carbonate. Further, 270 mL of sulfolane and 135 mL of toluene were added. The mixture was heated at 150° C. under reflux in a nitrogen atmosphere. Water resulting from the reaction was formed into an azeotropic mixture with toluene and was removed through the Dean-Stark tube. Water ceased to occur after 3 hours, and toluene was removed from the reaction system. The reaction liquid was stirred at 180° C. for 7 hours, and 15.1 g (60 mmol) of 4,4'-dichlorobenzophenone was added, followed by stirring for 3 hours.

The reaction liquid was left to cool, and inorganic matters insoluble in the reaction solution were removed by filtration with filter aid Celite. The filtrate was poured into 2.0 L of methanol to precipitate the reaction product. The precipitate was filtered, washed with a small amount of methanol, and vacuum dried. The dried product was redissolved in 150 mL of tetrahydrofuran. The solution was poured into 2.0 L of methanol to reprecipitate the product. The precipitate was filtered and vacuum dried to give 65 g of an objective compound (85% yield). The number average molecular weight

[Chem. 20]

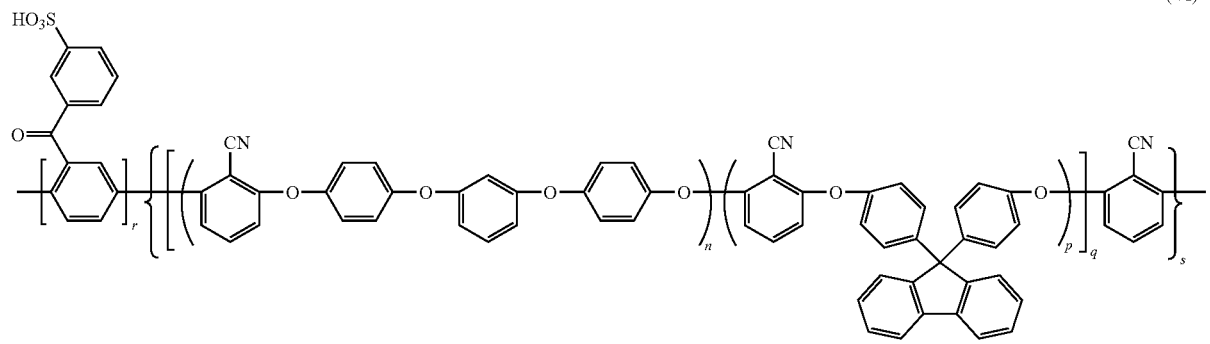

(VI)

and weight average molecular weight by GPC relative to polystyrene standards were 6400 and 7800, respectively. The compound was identified to be an oligomer represented by Formula (VII):

[Chem. 21]

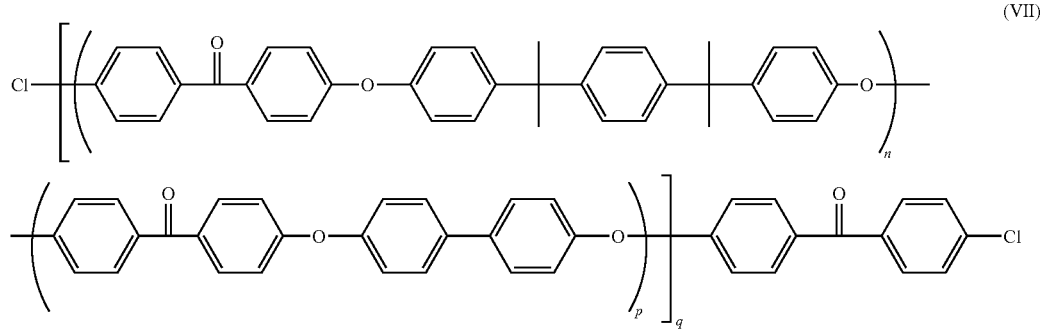

(VII)

(VII) The composition ratio of n and p was found to be n=0.60 and p=0.40.

Example 8

Synthesis of Sulfonated Polymer

A 1-liter three-necked flask equipped with a stirrer, a thermometer and a nitrogen inlet tube was charged with 56.8 g (141 mmol) of neopentyl 3-(2,5-dichlorobenzoyl)benzenesulfonate, 55.0 g (8.6 mmol) of the hydrophobic unit from Example 7 with Mn 6400, 2.94 g (5.0 mmol) of bis(triphenylphosphine)nickel dichloride, 0.67 g (5.0 mmol) of sodium iodide, 15.7 g (60 mmol) of triphenylphosphine and 23.5 g (360 mmol) of zinc. The flask was then purged with dry nitrogen. Subsequently, 280 mL of N,N-dimethylacetamide (DMAc) was added to the flask, and stirring was performed for 3 hours while maintaining the reaction temperature at 80° C. The reaction liquid was then diluted with 460 mL of DMAc, and insolubles were filtered.

The resultant solution was placed in a 2-liter three-necked flask equipped with a stirrer, a thermometer and a nitrogen inlet tube, and was heated to 115° C. with stirring. Subsequently, 24.6 g (285 mmol) of lithium bromide was added, followed by stirring for 7 hours. The resultant solution was poured into 5.0 L of acetone to precipitate the product. The product was sequentially washed with 1N hydrochloric acid and pure water in this order, and was dried to give 82 g of an objective polymer. The polymer had a weight average molecular weight (Mw) of 93000. The polymer was identified to be represented by Formula (VIII):

[Chem. 22]

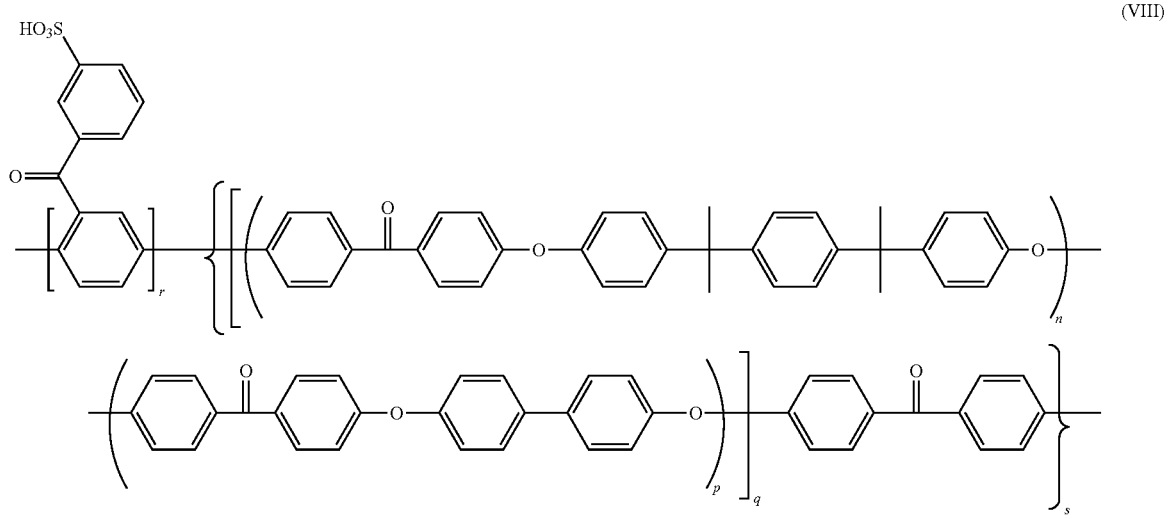

(VIII)

A 10 wt % N-methylpyrrolidone (NMP) solution of the sulfonated polymer was cast over a glass plate to give a film with a thickness of 40 μl.

Comparative Example 1

A 1-liter separable three-necked flask equipped with a stirring blade, a thermometer, a nitrogen inlet tube, a Dean-Stark tube and a condenser tube was charged with 50.2 g (200 mmol) of 4,4'-dichlorobenzophenone, 11.1 g (55.0 mmol) of 9,9-bis(4-hydroxyphenyl)fluorene, 57.8 g (165 mmol) of 4,4'-dihydroxydiphenyl ether and 39.5 g (286 mmol) of potassium carbonate. Further, 340 mL of sulfolane and 170 mL of toluene were added. The mixture was heated at 150° C. under reflux in a nitrogen atmosphere. Water resulting from the reaction was formed into an azeotropic mixture with toluene and was removed through the Dean-Stark tube. Water ceased to occur after 3 hours, and toluene was removed from the reaction system. The reaction liquid was stirred at 180° C. for 7 hours, and 10.0 g (40.0 mmol) of 4,4'-dichlorobenzophenone was added, followed by stirring for 3 hours.

The reaction liquid was left to cool, and inorganic matters insoluble in the reaction solution were removed by filtration with filter aid Celite. The filtrate was poured into 2.0 L of methanol to precipitate the reaction product. The precipitate was filtered, washed with a small amount of methanol, and vacuum dried. The dried product was redissolved in 150 mL of tetrahydrofuran. The solution was poured into 1.5 L of methanol to reprecipitate the product. The precipitate was filtered and vacuum dried to give 87 g of an objective compound (83% yield). The number average molecular weight and weight average molecular weight by GPC relative to polystyrene standards were 5500 and 8500, respectively. The compound was identified to be an oligomer represented by Formula (IX):

Comparative Example 2

Synthesis of Sulfonated Polymer

A 1-liter three-necked flask equipped with a stirrer, a thermometer and a nitrogen inlet tube was charged with 55.2 g (138 mmol) of neopentyl 3-(2,5-dichlorobenzoyl)benzenesulfonate, 67.9 g (12.3 mmol) of the hydrophobic unit from Comparative Example 1 with Mn 5500, 2.94 g (5.0 mmol) of bis(triphenylphosphine) nickel dichloride, 0.67 g (5.0 mmol) of sodium iodide, 15.7 g (60 mmol) of triphenylphosphine and 23.5 g (360 mmol) of zinc. The flask was then purged with dry nitrogen. Subsequently, 300 mL of N,N-dimethylacetamide (DMAc) was added to the flask, and stirring was performed for 3 hours while maintaining the reaction temperature at 80° C. The reaction liquid was then diluted with 520 mL of DMAc, and insolubles were filtered.

The resultant solution was placed in a 2-liter three-necked flask equipped with a stirrer, a thermometer and a nitrogen inlet tube, and was heated to 115° C. with stirring. Subsequently, 23.9 g (275 mmol) of lithium bromide was added, followed by stirring for 7 hours. The resultant solution was poured into 3.2 L of acetone to precipitate the product. The product was sequentially washed with 1N hydrochloric acid and pure water in this order, and was dried to give 88 g of an objective polymer. The polymer had a weight average molecular weight (Mw) of 93000. The polymer was identified to be represented by Formula (X):

[Chem. 23]

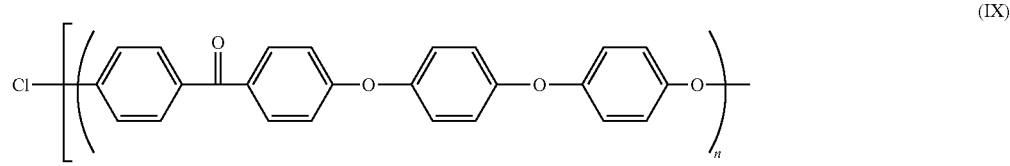

(IX)

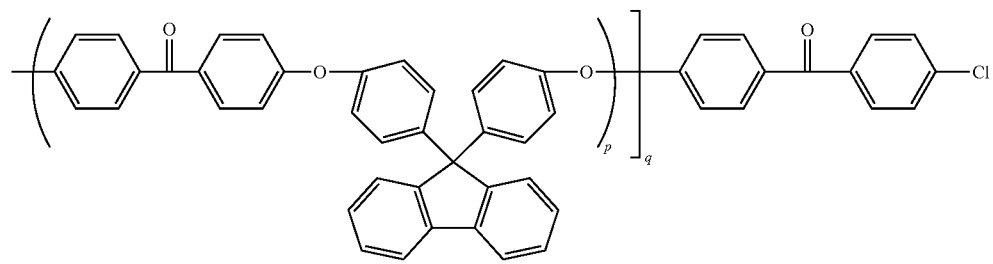

[Chem. 24]

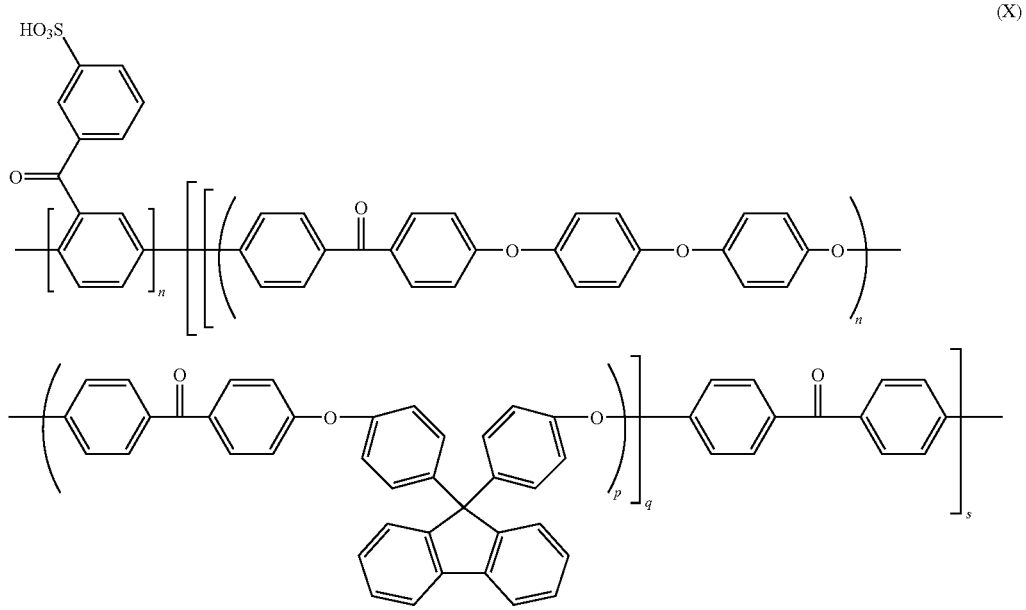

A 10 wt % N-methylpyrrolidone (NMP) solution of the sulfonated polymer was cast over a glass plate to give a film with a thickness of 40 μm.

[Evaluation]

The sulfonated polymers and films (proton conductive membranes) synthesized in Examples 2, 4, 6 and 8 and Comparative Example 2 were tested to evaluate properties. The results are shown in Table 1.

TABLE 1

|  |  | Ex. 2 | Ex. 4 | Ex. 6 | Ex. 8 | Comp. Ex. 2 |
|---|---|---|---|---|---|---|
| Ion exchange capacity | meq/g | 1.23 | 1.40 | 1.28 | 1.56 | 1.33 |
| Area percentage change | % | 168 | 133 | 126 | 140 | 137 |
| Methanol permeability | g/m²/h | 350 | 313 | 271 | 330 | 343 |
| Membrane resistance | Ω · cm² | 0.30 | 0.26 | 0.33 | 0.25 | 0.28 |
| Tg | °C. | 120 | 155 | 165 | 125 | 180 |
| Electrode joining properties |  | AA | AA | AA | AA | CC |

As shown in Table 1, the films obtained in Examples 2, 4, 6 and 8 achieved excellent electrode joining properties as well as low methanol permeability, low membrane resistance and good dimensional stability with aqueous methanol solution.

The invention claimed is:

1. A polyarylene copolymer comprising a structural unit represented by formula (1'):

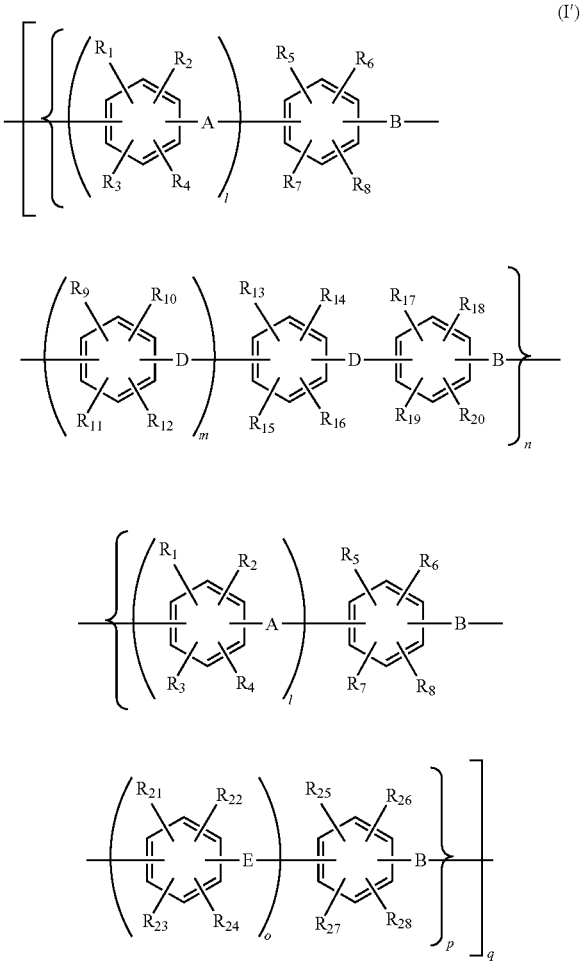

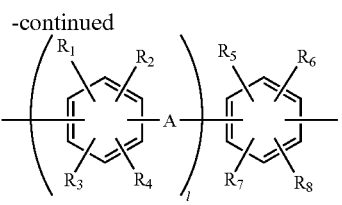

wherein
- A, D and E are each at least one structure selected from the group consisting of a direct bond, —O—, —S—, —CO—, —SO$_2$—, —SO—, —CONH—, —COO—, —(CF$_2$)$_f$— (wherein f is an integer of 1 to 10), —(CH$_2$)$_h$— (wherein h is an integer of 1 to 10), —CR'$_2$— (wherein R' is an aliphatic hydrocarbon group, an aromatic hydrocarbon group or a halogenated hydrocarbon group), a cyclohexylidene group and a fluorenylidene group, wherein D E;
- each B is independently an oxygen atom or a sulfur atom;
- R$_1$ to R$_{28}$ are the same or different from one another and are each at least one atom or group selected from the group consisting of a hydrogen atom, a fluorine atom, alkyl groups, partially or completely halogenated alkyl groups, allyl groups, aryl groups, nitro group and nitrile group;
- 1 and o are each an integer of 0 to 4;
- m is an integer of 1 to 4;
- q is an integer of 2 or greater;
- n and p indicate a composition ratio of the respective units and are each a number ranging from 0 to 1;
- n+p=1; and
- n is 0.3 to 0.75.

2. The polyarylene copolymer of claim 1, which has a glass transition temperature of 120 to 165° C.

3. The polyarylene copolymer of claim 1, which contains sulfonic acid groups.

4. The polyarylene copolymer of claim 1, which has a weight average molecular weight of 10,000 to 1,000,000.

5. The polyarylene copolymer of claim 1, which has a weight average molecular weight of 20,000 to 800,000.

6. The polyarylene copolymer of claim 1, which further comprises a structural unit represented by formula (6):

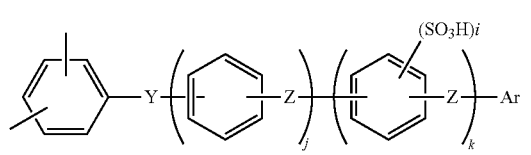

(6)

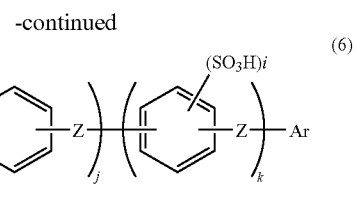

wherein
- Y is at least one structure selected from the group consisting of —CO—, —SO$_2$—, —SO—, —CONH—, —COO—, —(CF$_2$)$_f$— (wherein f is an integer of 1 to 10) and —C(CF$_3$)$_2$—;
- Z is at least one structure selected from the group consisting of a direct bond, —(CH$_2$)$_h$—(wherein h is an integer of 1 to 10), —C(CH$_3$)$_2$—, —O— and —S—;
- Ar is an aromatic group having a substituent represented by —SO$_3$H, —O(CH$_2$)$_r$SO$_3$H or —O(CF$_2$)$_r$SO$_3$H;
- r is an integer of 1 to 12;
- j is an integer of 0 to 10;
- k is an integer of 0 to 10; and
- i is an integer of 1 to 4.

7. The polyarylene copolymer of claim 6, wherein Y is CO— or —SO$_2$—.

8. The polyarylene copolymer of claim 6, wherein Ar is a phenyl or naphthyl group having a substituent represented by —SO$_3$H, —O(CH$_2$)$_r$SO$_3$H or —O(CF$_2$)$_r$SO$_3$H.

9. The polyarylene copolymer of claim 6, wherein Ar is a naphthyl group having two or more substituents represented by —SO$_3$H, —O(CH$_2$)$_r$SO$_3$H or —O(CF$_2$)$_r$SO$_3$H.

10. The polyarylene copolymer of claim 6, wherein j is 0, k is 0, Y is —CO—and Ar is a phenyl group having a substituent —SO$_3$H.

11. The polyarylene copolymer of claim 6, wherein j is 1, k is 0, Y is —CO—, Z is —O— and Ar is a phenyl group having a substituent —SO$_3$H.

12. The polyarylene copolymer of claim 6, wherein j is 1, k is 1, I is 1, Y is —CO—, Z is —O— and Ar is a phenyl group having a substituent —SO$_3$H.

13. The polyarylene copolymer of claim 6, wherein j is 1, k is 0, Y is —CO—, Z is —O—and Ar is a naphthyl group having two substituents —SO$_3$H.

14. The polyarylene copolymer of claim 6, wherein j is 1, k is 0, Y is —CO—, Z is O—and Ar is a phenyl group having a substituent —O(CH$_2$)$_4$SO$_3$H.

15. A solid polymer electrolyte comprising the polyarylene copolymer claim 6.

16. A proton conductive membrane comprising the polyarylene copolymer of claim 6.

17. A proton conductive membrane for direct methanol fuel cell comprising the polyarylene copolymer of claim 6.

* * * * *